(12) United States Patent
Zang et al.

(10) Patent No.: US 12,337,037 B2
(45) Date of Patent: Jun. 24, 2025

(54) TAXOL CONJUGATE COMPOUNDS, PHARMACEUTICAL COMPOSITIONS COMPRISING THE SAME, AND METHODS FOR THEIR USE

(71) Applicant: N1 Life, Inc, Milpitas, CA (US)

(72) Inventors: Xiaoyu Zang, Palo Alto, CA (US); Lin Cheng, Sunnyvale, CA (US)

(73) Assignee: N1 LIFE, INC., Milpitas, CA (US)

( * ) Notice: Subject to any disclaimer, the term of this patent is extended or adjusted under 35 U.S.C. 154(b) by 0 days.

(21) Appl. No.: 17/890,906

(22) Filed: Aug. 18, 2022

(65) Prior Publication Data

US 2023/0100247 A1 Mar. 30, 2023

Related U.S. Application Data

(60) Provisional application No. 63/235,073, filed on Aug. 19, 2021.

(51) Int. Cl.
*A61K 38/00* (2006.01)
*A61K 47/64* (2017.01)
*A61P 35/00* (2006.01)

(52) U.S. Cl.
CPC ............ *A61K 47/641* (2017.08); *A61P 35/00* (2018.01)

(58) Field of Classification Search
CPC ...... A61K 47/641; A61K 47/645; A61P 35/00
See application file for complete search history.

(56) References Cited

U.S. PATENT DOCUMENTS

| 2003/0083256 A1* | 5/2003 | Rothbard | A61P 37/08 |
| | | | 514/1.2 |
| 2011/0160146 A1* | 6/2011 | Wender | A61K 47/645 |
| | | | 435/375 |
| 2016/0128958 A1* | 5/2016 | Silverman | A61K 31/196 |
| | | | 435/375 |

FOREIGN PATENT DOCUMENTS

| WO | 02065986 A2 | 8/2002 |
| WO | 2008069824 A2 | 6/2008 |
| WO | 2009099636 A1 | 8/2009 |
| WO | 2023023276 A1 | 2/2023 |

OTHER PUBLICATIONS

Remington's Pharmaceutical Sciences, 18th Ed., Mack Publishing Co., Easton, Pa. (1990).*
International Search Report and The Written Opinion Of The International Searching Authority mailed Nov. 30, 2022, for International Patent Application No. PCT/US2022/040797, filed Aug. 18, 2022, 10 pages.
Kirschberg, T.A. et al. (2003, e-pub. Aug. 26, 2003). "Arginine-Based Molecular Transporters: The Synthesis And Chemical Evaluation Of Releasable Taxol-Transporter Conjugates," Organic Letters 5(19):3459-3462.

* cited by examiner

*Primary Examiner* — Jeanette M Lieb
(74) *Attorney, Agent, or Firm* — MORRISON & FOERSTER LLP

(57) ABSTRACT

Provided herein are Taxol transporter compounds, pharmaceutical compositions, methods of their preparation, and methods of their use in treatment or prevention of a proliferative, dermatological, or ophthalmological disease or disorder.

29 Claims, 14 Drawing Sheets

TAXOL CONJUGATE COMPOUNDS, PHARMACEUTICAL COMPOSITIONS COMPRISING THE SAME, AND METHODS FOR THEIR USE

This application claims the benefit of U.S. Provisional Application No. 63/235,073, filed Aug. 19, 2021, the entirety of which is incorporated herein by reference for all purposes.

Provided herein are Taxol conjugate compounds; pharmaceutical compositions comprising the compounds; methods of producing the compounds; and, methods of using the compounds and compositions for therapy. The compounds and compositions are useful, for instance, in methods of treatment, and prevention of proliferative, dermatological, or ophthalmological diseases or conditions, methods of detection of proliferative, dermatological, or ophthalmological diseases or conditions, and methods of diagnosis of proliferative, dermatological, or ophthalmological diseases or conditions.

BACKGROUND

Field

Despite many advances over many years, cancer remains a global health concern. Cancer is among the leading causes of death worldwide. In 2018, there were 18.1 million new cancer cases and 9.5 million cancer-related deaths worldwide. By 2040, the number of new cancer cases per year is expected to rise to 29.5 million and the number of cancer-related deaths to 16.4 million. See National Cancer Institute (US) and World Health Organization.

Liver cancer is common in sub-Saharan Africa and Southeast Asia. In many of these countries, it is the most common type of cancer. More than 800,000 people are diagnosed with this cancer each year throughout the world. Liver cancer is also a leading cause of cancer deaths worldwide, accounting for more than 700,000 deaths each year.

Ovarian cancer is the fifth leading cause of cancer death in females, with an estimated 22,000 women in the United States being diagnosed, accounting for 15,500 deaths.

Gastric cancer is the 4th most common cancer worldwide and the second leading cause of cancer death. 40% of gastric cancer deaths have liver metastasis, while 53-60% have peritoneal carcinomatosis. Systemic chemotherapy provides a median survival of 7 months; however with peritoneal spread the median survival is only 1-3 months.

Colorectal cancer is the third most common cancer diagnosed in the United States. It causes about 49,700 deaths annually, making it the second most common cause of cancer deaths. Approximately 10% of patients have peritoneal spread at the time diagnosis, and this is the second leading cause of death in patients with colorectal cancer. The median overall survival for patients with colorectal cancer with peritoneal dissemination is 24 months.

Currently, there are no chemotherapeutic agents specifically approved for intraperitoneal (IP) chemotherapy. All current IP chemotherapy clinical studies have been performed by off-label use of drugs designed for intravenous (IV) applications.

Dermatological diseases, on a global scale, are the fourth most common among all diseases, affecting almost one-third of the world population. Flohr, 2021, Brit. J. Dermatol. 184(2):189-190. As of 2013, skin diseases contributed 1.79% to the global burden of disease. Karimkhani et al., 2017, JAMA Dermatol. 153(5):406-412.

Ophthalmological conditions affect an estimated 2.2 billion people in the world as of 2021. Almost half of these cases could have been prevented or have yet to be addressed by treatment. The global burden of eye diseases was estimated to be 4.0% of the total global disease burden in 2013 as reported in Ono et al., 2010, Am. J. Public Health 100(9):1784-1788.

There is a need for additional therapies for treating proliferative, dermatological, or ophthalmological diseases and conditions. There is also a need for new therapies effective for intraperitoneal administration for treating proliferative, dermatological, or ophthalmological diseases and disorders.

SUMMARY

Provided herein are Taxol transporter conjugate compounds of Formula (I), and sub-formulas thereof, compositions comprising the compounds, methods of producing the compounds, and methods of using the compounds and compositions in treatment, and in diagnosis. The compounds of Formula (I) and sub-formulas and embodiments thereof, are useful for treating or preventing proliferative, dermatological, or ophthalmological disorders. In certain embodiments, the compounds can be used via intraperitoneal administration to treat or prevent proliferative, dermatological, or ophthalmological disorders. In certain embodiments, the compounds can be used via oral administration to treat or prevent proliferative disorders. The compounds of Formula (I) and sub-formulas and embodiments thereof, are useful for detection of proliferative, dermatological, or ophthalmological diseases or conditions, and for diagnosis of proliferative, dermatological, or ophthalmological diseases or conditions.

In one aspect, provided is a compound of Formula (I), or a pharmaceutically acceptable salt thereof:

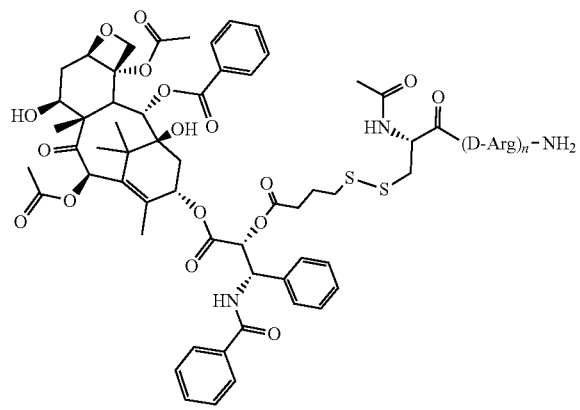

(I)

wherein n is an integer from 1-20.

The compounds comprise an acetylated L-cysteine amino acid residue bonded to (D-Arg)$_n$. The present description is based, at least in part, on the discovery of substantially improved properties in this compound compared to the corresponding compound comprising D-cysteine at the same position. In certain embodiments, the compounds provide improved water solubility compared to the D-cysteine compound. In certain embodiments, the compounds provide reduced P-glycoprotein interaction compared to the D-cysteine compound. In certain embodiments, the compounds provide prolonged drug release compared to the D-cysteine compound. As described in Biological Examples 2, 3, and 4, this is especially surprising because the unnatural D-amino acid is known to be resistant to protease cleavage. In certain embodiments, the compounds provide improved targeted drug release compared to the D-cysteine compound. In certain embodiments, the compounds provide improved potency against cancer cell lines compared to the D-cysteine compound. For example, as described in Biological Example 6, the tumor inhibitory rates of Compound 3 (the L-cysteine compound) when administered at 9.6 mg/kg was 90±8%, while the tumor inhibitory rate of Compound 5 (the D-cysteine compound) was only 79±11% when administered at the same dose. Further, under the dose and experimental conditions, Compound 3 had no obvious acute toxic effect on experimental mice, while Compound 5 caused animal death. In certain embodiments, the compounds provide improved potency against drug-resistant cancer cell lines compared to the D-cysteine compound. This is exemplified in Biological Example 2, wherein Compound 3 exhibited an $IC_{50}$ value of 437.5 nM against a multidrug-resistant breast cancer (MCF7/ADR) cell line, while Compound 5 exhibited an $IC_{50}$ of >1000 nM. In certain embodiments, the compounds provide a combination of these improvements or all of these improvements. In certain aspects, the compounds are useful in methods of treatment and prevention of proliferative, dermatological, or ophthalmological diseases.

In another aspect, provided are compositions comprising a compound of Formula (I). In some embodiments, the compositions are pharmaceutical compositions. Any suitable pharmaceutical composition may be used. In a further aspect, provided herein is a kit comprising the compound of Formula (I), or embodiments thereof, or a pharmaceutical composition thereof.

In another aspect, provided herein are methods of using the compounds or the compositions described herein. In some embodiments, the methods are for treatment. In some embodiments, the methods are diagnostic methods. In some embodiments, the methods are analytical methods. In some embodiments, the compounds, or compositions described herein are used to treat a disease or disorder. In some aspects, the disease or disorder is selected from a proliferative, dermatological, or ophthalmological disease and condition. In certain embodiments, the disease is cancer. In certain embodiments, the disease is dermatological. In certain embodiments, the disease is ophthalmological.

Also provided herein is the use of compounds described herein, and compositions thereof, for therapy. Also provided herein is the use of compounds described herein, and compositions thereof, for the treatment of a proliferative, dermatological, or ophthalmological disease or disorder. Also provided herein is the use of compounds described herein, and compositions thereof, for the manufacture of a medicament. Also provided herein is the use of compounds described herein, and compositions thereof, for the manufacture of a medicament for the treatment of a proliferative, dermatological, or ophthalmological disease or disorder. In certain embodiments, the disease is brain cancer, liver cancer, ovarian cancer, gastric cancer, or colorectal cancer. In certain embodiments, the disease is head and neck cancer, oral cancer, or maxillofacial cancer.

BRIEF DESCRIPTION OF THE FIGURES

FIG. 7 is a graph comparing the mice administered vehicle, the mice administered Taxol, and the mice administered Compound 5 to the mice administered Compound 3.

DESCRIPTION OF EXEMPLARY EMBODIMENTS

Figure 1:
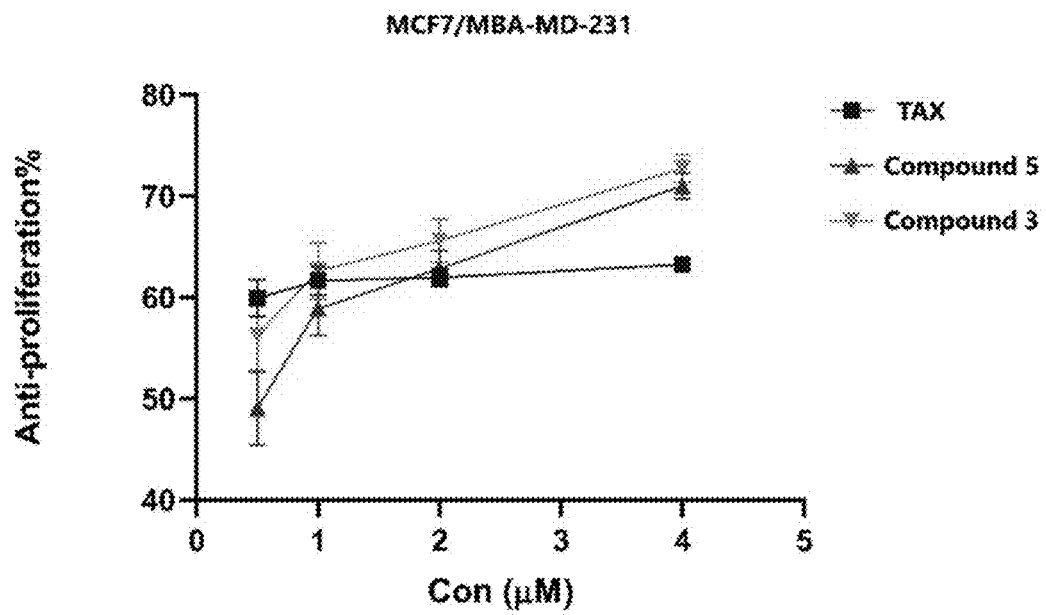
FIG. 1 provides anti-proliferation cell kill percent versus concentration for TAX (Taxol), Compound 5, and Compound 3 in MCF7/MBA-MD-231 cells as described in Biological Example 1.

Described herein are Taxol conjugate compounds useful for treating proliferative, dermatological, or ophthalmological diseases or conditions.

Definitions

Unless otherwise defined, all terms of art, notations and other scientific terminology used herein are intended to have the meanings commonly understood by those of skill in the art to which this disclosure pertains. In some cases, terms with commonly understood meanings are defined herein for clarity, and/or ready reference. The techniques and procedures described or referenced herein are generally well understood, and are commonly employed using conventional methodologies by those skilled in the art. As appropriate, procedures involving the use of commercially available kits, and reagents are generally carried out in accordance with manufacturer-defined protocols, and conditions unless otherwise noted.

As used herein, the singular forms "a," "an," and "the" include the plural referents unless the context clearly indicates otherwise.

The term "about" indicates and encompasses an indicated value, and a range above and below that value. In certain embodiments, the term "about" indicates the designated value±10%, ±5%, or ±1%. In certain embodiments, the term "about" indicates the designated value±one standard deviation of that value. In certain embodiments, for example, logarithmic scales (e.g., pH), the term "about" indicates the designated value±0.3, ±0.2, or ±0.1.

When referring to the compounds provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise.

The term "protecting group," as used herein, and unless otherwise specified, refers to a group that is added to an oxygen, nitrogen, or phosphorus atom to prevent its further reaction, or for other purposes. A wide variety of oxygen, and nitrogen protecting groups are known to those skilled in the art of organic synthesis. (See, e.g., Greene, et al., Protective Groups in Organic Synthesis, John Wiley and Sons, Fourth Edition, 2006, which is incorporated herein by reference).

"Pharmaceutically acceptable salt" refers to any salt of a compound provided herein which retains its biological properties, and which is not toxic or otherwise undesirable for pharmaceutical use. Such salts may be derived from a variety of organic, and inorganic counter-ions well known in the art. Such salts include, but are not limited to (1) acid addition salts formed with organic, or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, glutamic, hydroxynaphthoic, salicylic, stearic, cyclohexylsulfamic, quinic, muconic acid, and the like; or (2) salts formed when an acidic proton present in the parent compound either (a) is replaced by a metal ion, for example, an alkali metal ion, an alkaline earth ion, or an aluminum ion, or alkali metal, or alkaline earth metal hydroxides, such as sodium, potassium, calcium, magnesium, aluminum, lithium, zinc, and barium hydroxide, or ammonia; or (b) coordinates with an organic base, such as aliphatic, alicyclic, or aromatic organic amines, including, without limitation, ammonia, methylamine, dimethylamine, diethylamine, picoline, ethanolamine, diethanolamine, triethanolamine, ethylenediamine, lysine, arginine, ornithine, choline, N,N-dibenzylethylene-diamine, chloroprocaine, procaine, N-benzylphenethylamine, N-methylglucamine piperazine, tris(hydroxymethyl)-aminomethane, tetramethylammonium hydroxide, and the like.

Pharmaceutically acceptable salts further include, by way of example and without limitation, sodium, potassium, calcium, magnesium, ammonium, and tetraalkylammonium salts, and the like, and when the compound contains a basic functionality, salts of non-toxic organic, or inorganic acids, such as hydrohalides, for example, hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, glutamate, hydroxynaphthoate, salicylate, stearate, cyclohexylsulfamate, quinate, muconate, and the like.

The term "substantially free of" or "substantially in the absence of" with respect to a composition refers to a composition that includes at least 50%, 60%, 70%, 75%, 80%, 85%, or 90% by weight, in certain embodiments 95%, 98%, 99%, or 100% by weight; or in certain embodiments, 95%, 98%, 99%, or 100% of the designated enantiomer or diastereomer of a compound. In certain embodiments, in the methods and compounds provided herein, the compounds are substantially free of one of two enantiomers. In certain embodiments, in the methods and compounds provided herein, the compounds are substantially free of one of two diastereomers. In certain embodiments, in the methods and compounds provided herein, the compounds are substantially free of the opposite D-cysteine amino acid epimer.

The term "epimer" is one of a pair of diastereomers that have the opposite configuration at only one stereogenic center, or chiral center, out of at least two. For example, a compound of Formula (I) and the corresponding compound comprising a D-cysteine amino acid are epimers.

Similarly, the term "isolated" with respect to a composition refers to a composition that includes at least 50%, 60%, 70%, 75%, 85%, 90%, 95%, 98%, or 99% to 100% by weight, of the compound, the remainder comprising other chemical species, enantiomers or diastereomers.

As used herein, "enantiomeric excess (ee)" refers to a dimensionless mole ratio describing the purity of chiral substances that contain, for example, a single stereogenic center. For instance, an enantiomeric excess of zero would indicate a racemic (e.g., 50:50 mixture of enantiomers, or no excess of one enantiomer over the other). By way of further example, an enantiomeric excess of ninety-nine would indicate a nearly stereopure enantiomeric compound (i.e., large excess of one enantiomer over the other). The percentage enantiomeric excess, % ee=([(R)-compound]-[(S)-compound])/([(R)-compound]+[(S)-compound])×100, where the (R)-compound>(S)-compound; or % ee=([(S)-compound]-[(R)-compound])/([(S)-compound]+[(R)-compound])×100, where the (S)-compound>(R)-compound.

As used herein, "diastereomeric excess (de)" refers to a dimensionless mole ratio describing the purity of chiral substances that contain more than one stereogenic center. For example, a diastereomeric excess of zero would indicate an equimolar mixture of diastereoisomers. By way of further example, diastereomeric excess of ninety-nine would indicate a nearly stereopure diastereomeric compound (i.e., large excess of one diastereomer over the other). Diastereomeric excess may be calculated via a similar method to ee. As would be appreciated by a person of skill, de is usually reported as percent de (% de). % de may be calculated in a similar manner to % ee.

"Solvate" refers to a compound provided herein, or a salt thereof, that further includes a stoichiometric, or non-stoichiometric amount of solvent bound by non-covalent intermolecular forces. Where the solvent is water, the solvate is a hydrate.

"Isotopic composition" refers to the amount of each isotope present for a given atom, and "natural isotopic composition" refers to the naturally occurring isotopic composition, or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as hydrogen (H), the position is understood to have hydrogen at its natural isotopic composition.

"Isotopic enrichment" refers to the percentage of incorporation of an amount of a specific isotope at a given atom in a molecule in the place of that atom's natural isotopic abundance. For example, deuterium (D) enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

"Isotopically enriched" refers to an atom having an isotopic composition other than the natural isotopic composition of that atom. "Isotopically enriched" may also refer to a compound containing at least one atom having an isotopic composition other than the natural isotopic composition of that atom.

As used herein, term "$EC_{50}$" refers to a dosage, concentration, or amount of a particular test compound that elicits a dose-dependent response at 50% of maximal expression of a particular response that is induced, provoked, or potentiated by the particular test compound.

As used herein, and unless otherwise specified, the term "$IC_{50}$" refers to an amount, concentration, or dosage of a particular test compound that achieves a 50% inhibition of a maximal response in an assay that measures such response.

As used herein, the terms "subject", and "patient" are used interchangeably. The terms "subject", and "subjects" refer to an animal, such as a mammal including a non-primate (e.g., a cow, pig, horse, cat, dog, rat, and mouse), and a primate (e.g., a monkey, such as a cynomolgous monkey, a chimpanzee, and a human), and in certain embodiments, a human. In certain embodiments, the subject is a farm animal (e.g., a horse, a cow, a pig, etc.), or a pet (e.g., a dog or a cat). In certain embodiments, the subject is a human.

As used herein, the terms "therapeutic agent", and "therapeutic agents" refer to any agent(s) which can be used in the treatment, or prevention of a disorder, or one or more symptoms thereof. In certain embodiments, the term "therapeutic agent" includes a compound provided herein. In certain embodiments, a therapeutic agent is an agent which is known to be useful for, or has been, or is currently being used for the treatment, or prevention of a disorder, or one, or more symptoms thereof.

"Therapeutically effective amount" refers to an amount of a compound, or composition that, when administered to a subject for treating a condition, is sufficient to effect such treatment for the condition. A "therapeutically effective amount" can vary depending on, inter alia, the compound, the disease or disorder, and its severity, and the age, weight, etc., of the subject to be treated.

"Treating" or "treatment" of any disease, or disorder refers, in certain embodiments, to ameliorating a disease, or disorder that exists in a subject. In another embodiment, "treating", or "treatment" includes ameliorating at least one physical parameter, which may be indiscernible by the subject. In yet another embodiment, "treating", or "treatment" includes modulating the disease, or disorder, either physically (e.g., stabilization of a discernible symptom), or physiologically (e.g., stabilization of a physical parameter), or both. In yet another embodiment, "treating", or "treatment" includes delaying, or preventing the onset of the disease, or disorder, or delaying, or preventing recurrence of the disease, or disorder. In yet another embodiment, "treating", or "treatment" does not include preventing the onset of the disease, or disorder, or preventing recurrence of the disease, or disorder. In yet another embodiment, "treating", or "treatment" includes the reduction or elimination of either the disease, or disorder, or retarding the progression of the disease, or disorder, or of one, or more symptoms of the disease, or disorder, or reducing the severity of the disease, or disorder, or of one, or more symptoms of the disease, or disorder.

As used herein, the terms "prophylactic agent", and "prophylactic agents" as used refer to any agent(s) which can be used in the prevention of a disorder, or one or more symptoms thereof. In certain embodiments, the term "prophylactic agent" includes a compound provided herein. In certain other embodiments, the term "prophylactic agent" does not refer a compound provided herein. For example, a prophylactic agent is an agent which is known to be useful for, or has been or is currently being used to prevent, or impede the onset, development, progression, and/or severity of a disorder.

As used herein, the phrase "prophylactically effective amount" refers to the amount of a therapy (e.g., prophylactic agent) which is sufficient to result in the prevention, or reduction of the development, recurrence, or onset of one or more symptoms associated with a disorder, or to enhance or improve the prophylactic effect(s) of another therapy (e.g., another prophylactic agent).

Compounds of Formulae (I)-(II)

Provided herein are Taxol conjugate compounds useful for treating or preventing a proliferative, dermatological, or ophthalmological disease or disorder. The compounds can be prepared as described herein and used for therapy or diagnosis. In certain embodiments, the therapy is the treatment of a proliferative, dermatological, or ophthalmological disease or disorder.

The embodiments described herein include the recited compounds as well as pharmaceutically acceptable salts, hydrates, solvates, tautomers, and/or mixtures thereof.

In certain embodiments, provided is a compound of Formula (I), or a pharmaceutically acceptable salt, hydrate, solvate, tautomer, and/or mixture thereof:

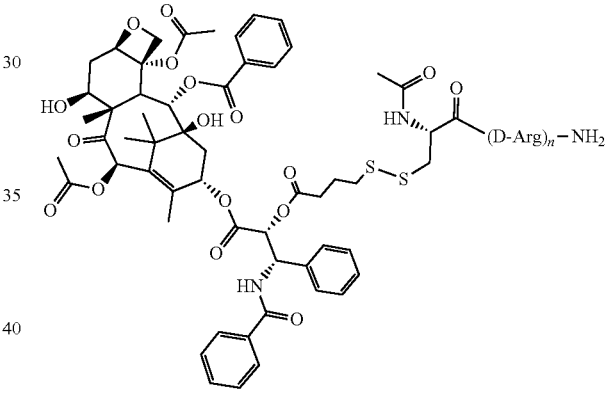

I wherein n is an integer selected from 1-20. In certain embodiments, n is 1. In certain embodiments, n is 2. In certain embodiments, n is 3. In certain embodiments, n is 4. In certain embodiments, n is 5. In certain embodiments, n is 6. In certain embodiments, n is 7. In certain embodiments, n is 8. In certain embodiments, n is 9. In certain embodiments, n is 10. In certain embodiments, n is 11. In certain embodiments, n is 12. In certain embodiments, n is 13. In certain embodiments, n is 14. In certain embodiments, n is 15. In certain embodiments, n is 16. In certain embodiments, n is 17. In certain embodiments, n is 18. In certain embodiments, n is 19. In certain embodiments, n is 20. In certain embodiments, n is an integer from 6-10. In preferred embodiments, n is 8.

In certain embodiments, provided is a compound of Formula (II), or a pharmaceutically acceptable salt, hydrate, solvate, tautomer, and/or mixture thereof:

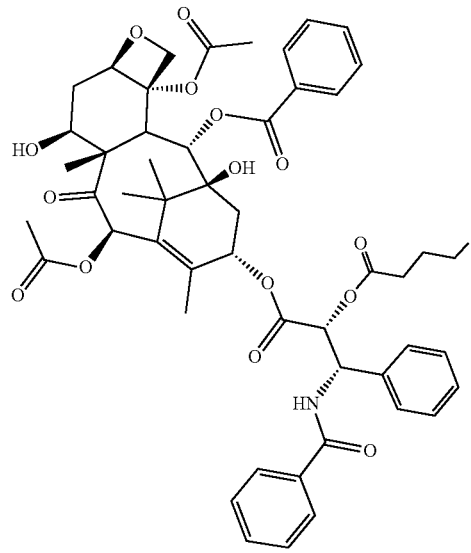
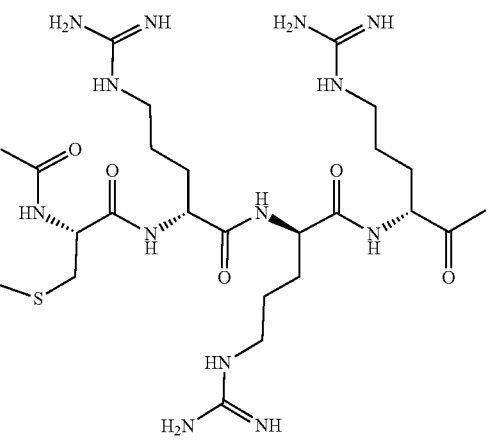
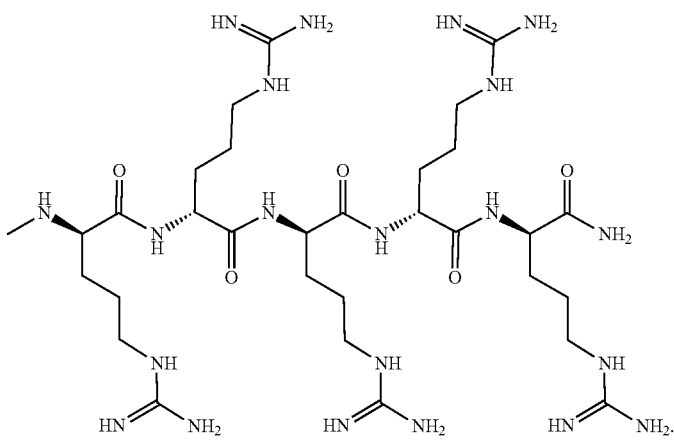

(II)

In certain embodiments, the compounds described herein have a de or % de greater than zero. For example, in certain embodiments, the compounds described herein have a de or % de of about ten. In certain embodiments, the compounds described herein have a de or % de of about twenty-five. In certain embodiments, the compounds described herein have a de or % de of about fifty. In certain embodiments, the compounds described herein have a de or % de of about seventy-five. In certain embodiments, the compounds described herein have a de or % de of about eighty. In certain embodiments, the compounds described herein have a de or % de of about eighty-five. In certain embodiments, the compounds described herein have a de or % de of about ninety. In certain embodiments, the compounds described herein have a de or % de of about ninety-five. In certain embodiments, the compounds described herein have a de or % de of about ninety-seven. In certain embodiments, the compounds described herein have a de or % de of about ninety-eight. In certain embodiments, the compounds described herein have a de or % de of about ninety-ninety. In certain embodiments, the compounds described herein have a de or % de of one-hundred.

In certain embodiments, the compound of Formula (I), or a pharmaceutically acceptable salt, hydrate, solvate, tautomer, and/or mixture thereof, is at least about 50% free, at least about 60% free, at least about 70% free, at least about 75% free, at least about 80% free, at least about 85% free, at least about 90% free, at least about 95% free, at least about 97% free, at least about 99% free, or 100% free by weight of the opposite D-cysteine amino acid epimer. In one embodiment, the compound of Formula (I), or a pharmaceutically acceptable salt, hydrate, solvate, tautomer, and/or mixture thereof, is about 85%-95% free of the opposite D-cysteine amino acid epimer. In one embodiment, the compound of Formula (I), or a pharmaceutically acceptable salt, hydrate, solvate, tautomer, and/or mixture thereof, is about 90%-95% free of the opposite D-cysteine amino acid epimer. In one embodiment, the compound of Formula (I), or a pharmaceutically acceptable salt, hydrate, solvate, tautomer, and/or mixture thereof, is at least about 85% free of the opposite D-cysteine amino acid epimer. In one embodiment, the compound of Formula (I), or a pharmaceutically acceptable salt, hydrate, solvate, tautomer, and/or mixture thereof, is at least about 90% free of the opposite D-cysteine amino acid epimer. In one embodiment, the compound of Formula (I), or a pharmaceutically acceptable salt, hydrate, solvate, tautomer, and/or mixture thereof, is at least about 95% free of the opposite D-cysteine amino acid epimer. In one embodiment, the compound of Formula (I), or a pharmaceutically acceptable salt, hydrate, solvate, tautomer, and/or mixture thereof, is at least about 97% free of the opposite D-cysteine amino acid epimer. In one embodiment, the compound of Formula (I), or a pharmaceutically acceptable salt, hydrate, solvate, tautomer, and/or mixture thereof, is 100% free of the opposite D-cysteine amino acid epimer.

In certain embodiments, the compound of Formula (II), or a pharmaceutically acceptable salt, hydrate, solvate, tautomer, and/or mixture thereof, is at least about 50% free, at least about 60% free, at least about 70% free, at least about 75% free, at least about 80% free, at least about 85% free, at least about 90% free, at least about 95% free, at least about 97% free, at least about 99% free, or 100% free by weight of the opposite D-cysteine amino acid epimer. In one embodiment, the compound of Formula (II), or a pharmaceutically acceptable salt, hydrate, solvate, tautomer, and/or mixture thereof, is about 85%-95% free of the opposite D-cysteine amino acid epimer. In one embodiment, the compound of Formula (II), or a pharmaceutically acceptable salt, hydrate, solvate, tautomer, and/or mixture thereof, is about 90%-95% free of the opposite D-cysteine amino acid epimer. In one embodiment, the compound of Formula (II), or a pharmaceutically acceptable salt, hydrate, solvate, tautomer, and/or mixture thereof, is at least about 85% free of the opposite D-cysteine amino acid epimer. In one embodiment, the compound of Formula (II), or a pharmaceutically acceptable salt, hydrate, solvate, tautomer, and/or mixture thereof, is at least about 90% free of the opposite D-cysteine amino acid epimer. In one embodiment, the compound of Formula (II), or a pharmaceutically acceptable salt, hydrate, solvate, tautomer, and/or mixture thereof, is at least about 95% free of the opposite D-cysteine amino acid epimer. In one embodiment, the compound of Formula (II), or a pharmaceutically acceptable salt, hydrate, solvate, tautomer, and/or mixture thereof, is at least about 97% free of the opposite D-cysteine amino acid epimer. In one embodiment, the compound of Formula (II), or a pharmaceutically acceptable salt, hydrate, solvate, tautomer, and/or mixture thereof, is 100% free of the opposite D-cysteine amino acid epimer.

In certain embodiments, provided is a compound of Formula (X), or a pharmaceutically acceptable salt, hydrate, solvate, tautomer, and/or mixture thereof:

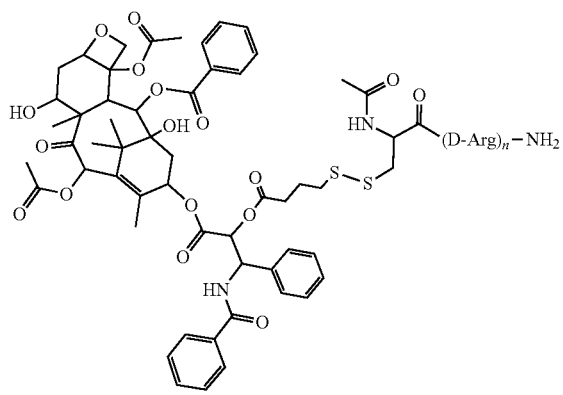

(X)

wherein the compound of Formula (X) comprises at least about 50%, at least about 60%, at least about 70%, at least about 75%, at least about 80%, at least about 85%, at least about 90%, at least about 95%, at least about 99%, or 100% by weight a compound of Formula (I):

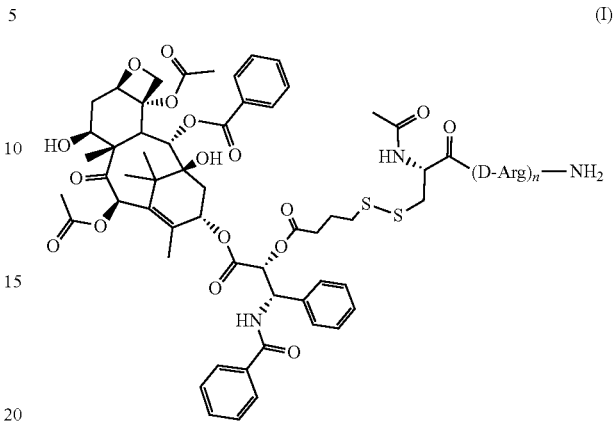

(I)

compared to the total weight of all stereoisomers of Formula (X);

wherein n is an integer selected from 1-20.

In certain embodiments, the compound of Formula (X) comprises at least about 50% or more by weight of a compound of Formula (I) compared to the total weight of all stereoisomers of Formula (X). In certain embodiments, the compound of Formula (X) comprises at least about 75% or more by weight of a compound of Formula (I) compared to the total weight of all stereoisomers of Formula (X). In certain embodiments, the compound of Formula (X) comprises at least about 80% or more by weight of a compound of Formula (I) compared to the total weight of all stereoisomers of Formula (X). In certain embodiments, the compound of Formula (X) comprises at least about 85% or more by weight of a compound of Formula (I) compared to the total weight of all stereoisomers of Formula (X). In certain embodiments, the compound of Formula (X) comprises at least about 90% or more by weight of a compound of Formula (I) compared to the total weight of all stereoisomers of Formula (X). In certain embodiments, the compound of Formula (X) comprises at least about 95% or more by weight of a compound of Formula (I) compared to the total weight of all stereoisomers of Formula (X). In certain embodiments, the compound of Formula (X) comprises at least about 97% or more by weight of a compound of Formula (I) compared to the total weight of all stereoisomers of Formula (X). In certain embodiments, the compound of Formula (X) comprises at least about 98% or more by weight of a compound of Formula (I) compared to the total weight of all stereoisomers of Formula (X). In certain embodiments, the compound of Formula (X) comprises at least about 99% or more by weight of a compound of Formula (I) compared to the total weight of all stereoisomers of Formula (X). In one embodiment, the compound of Formula (X) is 100% by weight a compound of Formula (I).

In certain embodiments, the compounds described herein have a de or % de range from about fifty to one hundred. In certain embodiments, the compounds described herein have a de or % de range from about sixty to one hundred. In certain embodiments, the compounds described herein have a de or % de range from about seventy to one hundred. In certain embodiments, the compounds described herein have a de or % de range from about seventy-five to one hundred. In certain embodiments, the compounds described herein have a de or % de range from about eighty to one hundred. In certain embodiments, the compounds described herein have a de or % de range from about eighty-five to one hundred. In certain embodiments, the compounds described herein have a de or % de range from about ninety to one hundred. In certain embodiments, the compounds described herein have a de or % de range from ninety-five to one hundred. In certain embodiments, the compounds described herein have a de or % de range from about ninety-seven to one hundred. In certain embodiments, the compounds described herein have a de or % de range from about ninety-eight to one hundred. In certain embodiments, the compounds described herein have a de or % de range from about ninety-nine to one hundred.

In some embodiments, provided herein are compositions of compounds of any of Formulas (I)-(II), that are substantially free of a designated stereoisomer of that compound. In some embodiments, provided herein are compositions of compounds of any of Formulas (I)-(II), that are substantially free of a designated stereoisomer of that compound wherein the designated stereoisomer is the opposite D-cysteine amino acid epimer. In certain embodiments, in the methods and compounds of this disclosure, the compounds are substantially free of other stereoisomers. In certain embodiments, in the methods and compounds of this disclosure, the compounds are substantially free of the opposite D-cysteine amino acid epimer. In some embodiments, the composition includes a compound that is at least about 50%, 60%, 70%, 75%, 85%, 90%, 95%, 98%, or 99% to 100% by weight of the compound, the remainder comprising other chemical species, or stereoisomers. In some embodiments, the composition includes a compound of Formula (I) or (II) that is at least about 50%, 60%, 70%, 75%, 85%, 90%, 95%, 98%, or 99% to 100% free of the opposite D-cysteine amino acid epimer by weight of the compound of Formula (I) or (II). In some embodiments, provided herein are compositions of compounds of any of Formulas (I)-(II), that are substantially free of a designated stereoisomer of that compound. In certain embodiments, in the methods and compounds of this disclosure, the compounds are substantially free of other stereoisomers. In some embodiments, the composition includes a compound that is at least about 50%, 60%, 70%, 75%, 85%, 90%, 95%, 98%, or 99% to 100% by weight of the compound, the remainder comprising other chemical species or stereoisomers.

Isotopically Enriched Compounds

Also provided herein are isotopically enriched compounds including, but not limited to, isotopically enriched compounds of any of Formulas (I)-(II).

Isotopic enrichment (for example, deuteration) of pharmaceuticals to improve pharmacokinetics ("PK"), pharmacodynamics ("PD"), and/or toxicity profiles, has been previously demonstrated within some classes of drugs. See, for example, Lijinsky et al., Food Cosmet. Toxicol., 20: 393 (1982); Lijinsky et al., J. Nat. Cancer Inst., 69: 1127 (1982); Mangold et al., Mutation Res. 308: 33 (1994); Gordon et al., Drug Metab. Dispos., 15: 589 (1987); Zello et al., Metabolism, 43: 487 (1994); Gately et al., J. Nucl. Med., 27: 388 (1986); Wade D, Chem. Biol. Interact. 117: 191 (1999).

Isotopic enrichment of a drug can be used, for example, to (1) reduce or eliminate unwanted metabolites; (2) increase the half-life of the parent drug; (3) decrease the number of doses needed to achieve a desired effect; (4) decrease the amount of a dose necessary to achieve a desired effect; (5) increase the formation of active metabolites if any are formed; and/or (6) decrease the production of deleterious metabolites in specific tissues. Isotopic enrichment of a drug can also be used to create a more effective and/or safer drug for combination therapy, whether the combination therapy is intentional or not.

Replacement of an atom for one of its isotopes often will result in a change in the reaction rate of a chemical reaction. This phenomenon is known as the Kinetic Isotope Effect ("ME"). For example, if a C—H bond is broken during a rate-determining step in a chemical reaction (i.e., the step with the highest transition state energy), substitution of a (heavier) isotope for that reactive hydrogen will cause a decrease in the reaction rate. The Deuterium Kinetic Isotope Effect ("DME") is the most common form of KIE. (See, e.g., Foster et al., Adv. Drug Res., vol. 14, pp. 1-36 (1985); Kushner et al., Can. J. Physiol. Pharmacol., vol. 77, pp. 79-88 (1999)).

The magnitude of the DME can be expressed as the ratio between the rates of a given reaction in which a C—H bond is broken, and the same reaction where deuterium is substituted for hydrogen and the C-D bond is broken. The DME can range from about one (no isotope effect) to very large numbers, such as 50, or more, meaning that the reaction can be fifty, or more, times slower when deuterium has been substituted for hydrogen.

Substitution of tritium ("T") for hydrogen results in yet a stronger bond than deuterium and gives numerically larger isotope effects. Similarly, substitution of isotopes for other elements including, but not limited to, $^{13}C$, or $^{14}C$ for carbon; $^{33}S$, $^{34}S$, or $^{36}S$ for sulfur; $^{15}N$ for nitrogen; and $^{17}O$, or $^{18}O$ for oxygen may lead to a similar kinetic isotope effect.

The mammal body expresses a variety of enzymes for the purpose of eliminating foreign substances, such as therapeutic agents, from its circulation system. Examples of such enzymes include the cytochrome P450 enzymes ("CYPs"), esterases, proteases, reductases, dehydrogenases, and monoamine oxidases to react with and convert these foreign substances to more polar intermediates, or metabolites for renal excretion. Some of the most common metabolic reactions of pharmaceutical compounds involve the oxidation of a carbon-hydrogen (C—H) bond to either a carbon-oxygen (C—O), or carbon-carbon (C═C) pi-bond. The resultant metabolites may be stable, or unstable under physiological conditions, and can have substantially different PK/PD, and acute, and long-term toxicity profiles relative to the parent compounds. For many drugs, such oxidations are rapid. Therefore, these drugs often require the administration of multiple or high daily doses.

Therefore, isotopic enrichment at certain positions of a compound provided herein will produce a detectable ME that will affect the pharmacologic, PK, PD, and/or toxicological profiles of a compound provided herein in comparison with a similar compound having a natural isotopic composition.

Compositions and Uses

Pharmaceutical Compositions and Methods of Administration

The compounds provided herein can be formulated into pharmaceutical compositions using methods available in the art and those disclosed herein. Any of the compounds provided herein can be provided in the appropriate pharmaceutical composition and be administered by a suitable route of administration. In one embodiment, a pharmaceutical composition is provided that comprises a compound of Formula (X) wherein the composition comprises at least about 50%, at least about 60%, at least about 70%, at least about 75%, at least about 80%, at least about 85%, at least about 90%, at least about 95%, at least about 99%, or 100% by weight a compound of Formula (I) compared to the total weight of all stereoisomers of Formula (X) and one, or more pharmaceutically acceptable carriers, excipients, or diluents.

In one embodiment, a pharmaceutical composition is provided that comprises a compound of Formula (I) wherein the composition is at least about 50% free, at least about 60% free, at least about 70% free, at least about 75% free, at least about 80% free, at least about 85% free, at least about 90% free, at least about 95% free, at least about 99% free, or 100% free by weight of the opposite D-cysteine amino acid epimer and one, or more pharmaceutically acceptable carriers, excipients, or diluents. In one embodiment, the pharmaceutical composition that comprises a compound of Formula (I) is about 85%-95% free by weight of the opposite D-cysteine amino acid epimer. In one embodiment, the pharmaceutical composition that comprises a compound of Formula (I) is about 90%-95% free by weight of the opposite D-cysteine amino acid epimer. In one embodiment, the pharmaceutical composition that comprises a compound of Formula (I) is about 85% free by weight of the opposite D-cysteine amino acid epimer. In one embodiment, the pharmaceutical composition that comprises a compound of Formula (I) is about 90% free by weight of the opposite D-cysteine amino acid epimer. In one embodiment, the pharmaceutical composition that comprises a compound of Formula (I) is about 95% free by weight of the opposite D-cysteine amino acid epimer. In one embodiment, the pharmaceutical composition that comprises a compound of Formula (I) is about 97% free by weight of the opposite D-cysteine amino acid epimer. In one embodiment, the pharmaceutical composition that comprises a compound of Formula (I) is 100% free by weight of the opposite D-cysteine amino acid epimer.

In one embodiment, a pharmaceutical composition is provided that comprises a compound of Formula (II) wherein the composition is at least about 50% free, at least about 60% free, at least about 70% free, at least about 75% free, at least about 80% free, at least about 85% free, at least about 90% free, at least about 95% free, at least about 99% free, or 100% free by weight of the opposite D-cysteine amino acid epimer and one, or more pharmaceutically acceptable carriers, excipients, or diluents. In one embodiment, the pharmaceutical composition that comprises a compound of Formula (II) is about 85%-95% free by weight of the opposite D-cysteine amino acid epimer. In one embodiment, the pharmaceutical composition that comprises a compound of Formula (II) is about 90%-95% free by weight of the opposite D-cysteine amino acid epimer. In one embodiment, the pharmaceutical composition that comprises a compound of Formula (II) is about 85% free by weight of the opposite D-cysteine amino acid epimer. In one embodiment, the pharmaceutical composition that comprises a compound of Formula (II) is about 90% free by weight of the opposite D-cysteine amino acid epimer. In one embodiment, the pharmaceutical composition that comprises a compound of Formula (II) is about 95% free by weight of the opposite D-cysteine amino acid epimer. In one embodiment, the pharmaceutical composition that comprises a compound of Formula (II) is about 97% free by weight of the opposite D-cysteine amino acid epimer. In one embodiment, the pharmaceutical composition that comprises a compound of Formula (II) is 100% free by weight of the opposite D-cysteine amino acid epimer.

The methods provided herein encompass administering pharmaceutical compositions comprising at least one compound provided herein and one or more compatible and pharmaceutically acceptable carriers. In this context, the term "pharmaceutically acceptable" means approved by a regulatory agency of the Federal, or state government, or listed in the U.S. Pharmacopeia, or other generally recognized pharmacopeia for use in animals, and in certain embodiments in humans. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils including petroleum, animal, vegetable, or oils of synthetic origin, such as peanut oil, soybean oil, mineral oil, sesame oil, and the like. Water can be used as a carrier when the pharmaceutical composition is administered intravenously. Saline solutions, and aqueous dextrose, and glycerol solutions can also be employed as liquid carriers, particularly for injectable solutions. Examples of suitable pharmaceutical carriers are described in Martin, E. W., *Remington's Pharmaceutical Sciences*.

In clinical practice the pharmaceutical compositions or compounds provided herein may be administered by any route known in the art. Exemplary routes of administration include, but are not limited to, oral, inhalation, sublingual, buccal, intraarterial, intradermal, intramuscular, intraperitoneal, intravenous, nasal, parenteral, pulmonary, and subcutaneous routes. In some embodiments, a pharmaceutical composition or compound provided herein is administered parenterally. In some embodiments, a pharmaceutical composition or compound provided herein is administered orally.

The compositions for parenteral administration can be emulsions or sterile solutions. Parenteral compositions may include, for example, propylene glycol, polyethylene glycol, vegetable oils, and injectable organic esters (e.g., ethyl oleate). These compositions can also contain wetting, isotonizing, emulsifying, dispersing, and stabilizing agents. Sterilization can be carried out in several ways, for example, using a bacteriological filter, via radiation, or via heating. Parenteral compositions can also be prepared in the form of sterile solid compositions which can be dissolved at the time of use in sterile water, or any other injectable sterile medium.

In some embodiments, a composition provided herein is a pharmaceutical composition or a single unit dosage form. Pharmaceutical compositions, and single unit dosage forms provided herein comprise a prophylactically, or therapeutically effective amount of one, or more prophylactic, or therapeutic compounds.

The pharmaceutical composition may comprise one or more pharmaceutical excipients. Any suitable pharmaceutical excipient may be used, wherein a person of ordinary skill in the art is capable of selecting suitable pharmaceutical excipients. Non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. Whether a particular excipient is suitable for incorporation into a pharmaceutical composition, or dosage form depends on a variety of factors well known in the art including, but not limited to, the way in which the dosage form will be administered to a subject and the specific compound in the dosage form. The composition, or single unit dosage form, if desired, can also contain minor amounts of wetting, or emulsifying agents, or pH buffering agents. Accordingly, the pharmaceutical excipients provided below are intended to be illustrative, and not limiting. Additional pharmaceutical excipients include, for example, those described in the

*Handbook of Pharmaceutical Excipients*, Rowe et al. (Eds.) 6th Ed. (2009), incorporated by reference herein in its entirety.

In some embodiments, the pharmaceutical composition comprises an anti-foaming agent. Any suitable anti-foaming agent may be used. In some aspects, the anti-foaming agent is selected from an alcohol, an ether, an oil, a wax, a silicone, a surfactant, and combinations thereof. In some aspects, the anti-foaming agent is selected from a mineral oil, a vegetable oil, ethylene bis stearamide, a paraffin wax, an ester wax, a fatty alcohol wax, a long-chain fatty alcohol, a fatty acid soap, a fatty acid ester, a silicon glycol, a fluorosilicone, a polyethylene glycol-polypropylene glycol copolymer, polydimethylsiloxane-silicon dioxide, ether, octyl alcohol, capryl alcohol, sorbitan trioleate, ethyl alcohol, 2-ethyl-hexanol, dimethicone, oleyl alcohol, simethicone, and combinations thereof.

In some embodiments, the pharmaceutical composition comprises a co-solvent. Illustrative examples of co-solvents include, for example, ethanol, poly(ethylene) glycol, butylene glycol, dimethylacetamide, glycerin, and propylene glycol.

In some embodiments, the pharmaceutical composition comprises a buffer. Illustrative examples of buffers include, for example, acetate, borate, carbonate, lactate, malate, phosphate, citrate, hydroxide, diethanolamine, monoethanolamine, glycine, methionine, guar gum, and monosodium glutamate.

In some embodiments, the pharmaceutical composition comprises a carrier or filler. Illustrative examples of carriers, or fillers, include, for example, lactose, maltodextrin, mannitol, sorbitol, chitosan, stearic acid, xanthan gum, and guar gum.

In some embodiments, the pharmaceutical composition comprises a surfactant. Illustrative examples of surfactants include, for example, d-alpha tocopherol, benzalkonium chloride, benzethonium chloride, cetrimide, cetylpyridinium chloride, docusate sodium, glyceryl behenate, glyceryl monooleate, lauric acid, macrogol 15 hydroxystearate, myristyl alcohol, phospholipids, polyoxyethylene alkyl ethers, polyoxyethylene sorbitan fatty acid esters, polyoxyethylene stearates, polyoxylglycerides, sodium lauryl sulfate, sorbitan esters, and vitamin E polyethylene(glycol) succinate.

In some embodiments, the pharmaceutical composition comprises an anti-caking agent. Illustrative examples of anti-caking agents include, for example, calcium phosphate (tribasic), hydroxymethyl cellulose, hydroxypropyl cellulose, and magnesium oxide.

Other excipients that may be used with the pharmaceutical compositions include, for example, albumin, antioxidants, antibacterial agents, antifungal agents, bioabsorbable polymers, chelating agents, controlled release agents, diluents, dispersing agents, dissolution enhancers, emulsifying agents, gelling agents, ointment bases, penetration enhancers, preservatives, solubilizing agents, solvents, stabilizing agents, and sugars. Specific examples of each of these agents are described, for example, in the *Handbook of Pharmaceutical Excipients*, Rowe et al. (Eds.) 6th Ed. (2009), The Pharmaceutical Press, incorporated by reference herein in its entirety.

In some embodiments, the pharmaceutical composition comprises a solvent. In some aspects, the solvent is saline solution, such as a sterile isotonic saline solution, or dextrose solution. In some aspects, the solvent is water for injection.

In some embodiments, the pharmaceutical compositions are in a particulate form, such as a microparticle or a nanoparticle. Microparticles and nanoparticles may be formed from any suitable material, such as a polymer, or a lipid. In some aspects, the microparticles or nanoparticles are micelles, liposomes, or polymersomes.

Further provided herein are anhydrous pharmaceutical compositions and dosage forms comprising a compound, since, in some embodiments, water can facilitate the degradation of some compounds.

Anhydrous pharmaceutical compositions and dosage forms provided herein can be prepared using anhydrous, or low moisture containing ingredients, and low moisture, or low humidity conditions. Pharmaceutical compositions and dosage forms that comprise lactose and at least one active ingredient that comprises a primary or secondary amine can be anhydrous if substantial contact with moisture and/or humidity is made during manufacturing, packaging, and/or storage is expected.

An anhydrous pharmaceutical composition can be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Lactose-free compositions provided herein can comprise excipients that are well known in the art and are listed, for example, in the U.S. Pharmocopeia (USP) SP (III)/NF (XVI). In general, lactose-free compositions comprise an active ingredient, a binder/filler, and a lubricant in pharmaceutically compatible and pharmaceutically acceptable amounts. Exemplary lactose-free dosage forms comprise an active ingredient, microcrystalline cellulose, pre gelatinized starch, and magnesium stearate.

Also provided are pharmaceutical compositions and dosage forms that comprise one or more excipients that reduce the rate by which a compound will decompose. Such excipients, which are referred to herein as "stabilizers," include, but are not limited to, antioxidants such as ascorbic acid, pH buffers, or salt buffers.

Parenteral Dosage Forms

In certain embodiments, provided are parenteral dosage forms. Parenteral dosage forms can be administered to subjects by various routes including, but not limited to, subcutaneous, intravenous (including bolus injection), inhalation, intramuscular, and intraarterial. Because their administration typically bypasses subjects' natural defenses against contaminants, parenteral dosage forms are typically sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, emulsions, and atomized droplets ready to be inhaled.

Suitable vehicles that can be used to provide parenteral dosage forms are well known to those skilled in the art. Examples include, but are not limited to Water for Injection USP; aqueous vehicles such as, but not limited to, Sodium Chloride Injection, Ringer's Injection, Dextrose Injection, Dextrose, and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Dosage forms for drug delivery via inhalation include propellants, non-aqueous inhalers, dry powder inhalers, and jet or ultrasonic nebulizers.

Excipients that increase the solubility of one or more of the compounds disclosed herein can also be incorporated into the parenteral dosage forms.

Oral Dosage Forms

In certain embodiments, provided are oral dosage forms. Oral dosage forms can be administered to subjects by various routes including, but not limited to, sublingual, sublabial, and buccal. Typical dosage forms for oral administration includes a pill, a tablet, a capsule, a gel cap, a solution, a suspension, or an emulsion. The dosage form may also feature compartmentalization. For example, when the dosage form is a pill, tablet, or capsule, it may have different layers of material which have different excipients or different concentrations of excipients. For example, an enteric coated oral tablet may be used to enhance bioavailability of the compounds for an oral route of administration. The enteric coating will be a layer of excipient that allows the tablet to survive stomach acid. In one embodiment, the oral dosage form is an oral disintegrating tablet. In one embodiment, the oral dosage form is a chewable tablet.

Dosage and Unit Dosage Forms

In human therapeutics, the doctor will determine the posology which he considers most appropriate according to a preventive, or curative treatment, and according to the age, weight, condition, and other factors specific to the subject to be treated.

In certain embodiments, a composition provided herein is a pharmaceutical composition or a single unit dosage form. Pharmaceutical compositions and single unit dosage forms provided herein comprise a prophylactically, or therapeutically effective amount of one or more prophylactic, or therapeutic compounds described herein.

The amount of the compound or composition which will be effective in the prevention or treatment of a disorder, or one or more symptoms thereof, will vary with the nature and severity of the disease or disorder and the route by which the compound is administered. The frequency and dosage will also vary according to factors specific for each subject depending on the specific therapy (e.g., therapeutic or prophylactic agents) administered, the severity of the disorder, disease or disorder, and the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the compound per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). In certain embodiments, the dosage of the compound provided herein, based on weight of the compound, administered to prevent, treat, manage, or ameliorate a disorder or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to prevent, treat, manage, or ameliorate a disorder, or one or more symptoms thereof in a subject is 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.25 mg to 2.5 mg, 0.5 mg to 20 mg, 0.5 to 15 mg, 0.5 to 12 mg, 0.5 to 10 mg, 0.5 mg to 7.5 mg, 0.5 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

The dose can be administered according to a suitable schedule, for example, once, two times, three times, or four times weekly. It may be necessary to use dosages of the compound outside the ranges disclosed herein in some cases, as will be apparent to those of ordinary skill in the art. Furthermore, it is noted that the clinician, or treating physician will know how, and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat, or ameliorate such disorders, but insufficient to cause, or sufficient to reduce, adverse effects associated with the compounds or compositions provided herein are also encompassed by the described dosage amounts and dose frequency schedules herein. Further, when a subject is administered multiple dosages of a composition provided herein, not all of the dosages need be the same. For example, the dosage administered to the subject may be increased to improve the prophylactic or therapeutic effect of the composition, or it may be decreased to reduce one or more side effects that a particular subject is experiencing.

In certain embodiments, treatment or prevention can be initiated with one or more loading doses of a compound or composition provided herein followed by one or more maintenance doses.

In certain embodiments, a dose of a compound or composition provided herein can be administered to achieve a steady-state concentration of the compound in blood or serum of the subject. The steady-state concentration can be determined by measurement according to techniques available to those of skill or can be based on the physical characteristics of the subject such as height, weight, and age.

In certain embodiments, administration of the same composition may be repeated and the administrations may be separated by at least one day, two days, three days, five days, ten days, fifteen days, thirty days, forty-five days, two months, seventy-five days, three months, or six months. In other embodiments, administration of the same prophylactic or therapeutic agent may be repeated, and the administration may be separated by at least one day, two days, three days, five days, ten days, fifteen days, thirty days, forty-five days, two months, seventy-five days, three months, or six months.

Therapeutic Applications

For therapeutic applications, the compounds are administered to a mammal, in certain embodiments, a human, in a pharmaceutically acceptable dosage suitable for administration form such as those known in the art, and those discussed herein, intravenously as a bolus or by continuous infusion over a period of time, by intramuscular, intraperitoneal, intra-cerebrospinal, subcutaneous, intra-articular, intrasynovial, intrathecal, inhalation, or intratumoral routes. The compounds also are suitably administered by peritumoral, intralesional, or perilesional routes, to exert local as well as systemic therapeutic effects. In certain embodiments, the compounds are administered to a mammal, in certain embodiments, a human, in a pharmaceutically acceptable dosage suitable for oral administration form such as those known in the art, and those discussed herein, for example sublingually. For example, the compounds of this disclosure may be administered orally to a human as a liquid or solid form. Solid dosage forms include, for example, capsules, tablets, pills, powders, and granules. In such solid dosage forms, the chemical entity is mixed with one or more pharmaceutically acceptable excipients, such as sodium citrate or dicalcium phosphate and/or: a) fillers or extenders such as, for example, starches, lactose, sucrose, glucose, mannitol, and silicic acid, b) binders such as, for example, carboxymethylcellulose, alginates, gelatin, polyvinylpyrrolidinone, sucrose, and acacia, c) humectants such as, for example, glycerol, d) disintegrating agents such as, for example, agar-agar, calcium carbonate, potato or tapioca starch, alginic acid, certain silicates, and sodium carbonate, e) solution retarding agents such as, for example, paraffin, f) absorption accelerators such as, for example, quaternary ammonium compounds, g) wetting agents such as, for example, cetyl alcohol and glycerol monostearate, h) absorbents such as, for example, kaolin and bentonite clay, and i) lubricants such as, for example, talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like. In one embodiment, the oral dosage form is an oral disintegrating tablet.

The compounds provided herein may be useful for the treatment of any disease or disorder described herein (e.g., a proliferative, dermatological, or ophthalmological disease or disorder).

In certain embodiments, the disease or disorder is cancer. In certain embodiments, the disease or disorder is brain cancer, liver cancer, ovarian cancer, gastric cancer, or colorectal cancer. In certain embodiments, the disease or disorder is brain cancer. In certain embodiments, the disease or disorder is liver cancer. In certain embodiments, the disease or disorder is ovarian cancer. In certain embodiments, the disease or disorder is gastric cancer. In certain embodiments, the disease or disorder is colorectal cancer.

In certain embodiments, the disease or disorder is head and neck cancer, oral cancer, or maxillofacial cancer.

Suitable examples of cancer include, breast cancer (e.g., invasive ductal breast cancer, noninvasive ductal breast cancer, inflammatory breast cancer), prostate cancer (e.g., hormone-dependent prostate cancer, hormone-independent prostate cancer), pancreatic cancer (e.g., ductal pancreatic cancer), gastric cancer (e.g., papillary adenocarcinoma, mucous adenocarcinoma, adenosquamous carcinoma), lung cancer (e.g., non-small cell lung cancer, small-cell lung cancer, malignant mesothelioma), colon cancer (e.g., gastrointestinal stromal tumor), rectal cancer (e.g., gastrointestinal stromal tumor), colorectal cancer (e.g., familial colorectal cancer, hereditary non-polyposis colorectal cancer, gastrointestinal stromal tumor), small intestinal cancer (e.g., non-Hodgkin's lymphoma, gastrointestinal stromal tumor), esophageal cancer, duodenal cancer, tongue cancer, pharyngeal cancer (e.g., nasopharyngeal cancer, oropharynx cancer, hypopharyngeal cancer), salivary gland cancer, brain tumor (e.g., pineal astrocytoma, pilocytic astrocytoma, diffuse astrocytoma, anaplastic astrocytoma), neurilemmoma, liver cancer (e.g., primary liver cancer, extrahepatic bile duct cancer), renal cancer (e.g., renal cell cancer, transitional cell cancer of the renal pelvis and ureter), bile duct cancer, endometrial cancer, uterine cervical cancer, ovarian cancer (e.g., epithelial ovarian cancer, extragonadal germ cell tumor, ovarian germ cell tumor, ovarian tumor of low malignant potential), bladder cancer, urethral cancer, skin cancer (e.g., intraocular (ocular) melanoma, Merkel cell carcinoma), hemangioma, malignant lymphoma, malignant melanoma, thyroid cancer (e.g., medullary thyroid cancer), parathyroid cancer, nasal cavity cancer, sinus cancer, bone tumor (e.g., osteosarcoma, Ewing tumor, uterine sarcoma, soft tissue sarcoma), angiofibroma, sarcoma of the retina, penis cancer, testicular tumor, pediatric solid tumor (e.g., Wilms' tumor, childhood kidney tumor), Kaposi's sarcoma, Kaposi's sarcoma caused by AIDS, tumor of maxillary sinus, fibrous histiocytoma, leiomyosarcoma, rhabdomyosarcoma, and leukemia (e.g., acute myeloid leukemia, acute lymphoblastic leukemia).

In certain embodiments, the disease is dermatological. In certain embodiments, the disease is selected from the group consisting of, acne scarring, actinic keratosis, age spots (liver spots), atopic dermatitis (eczema), autoimmune diseases, basal cell carcinoma, bullous pemphigoid, burning mouth syndrome, calciphylaxis, cancer, canker sore, chronic hives, connective tissue disorders, contact dermatitis, cutaneous lupus, cutaneous T-cell lymphoma, dermatitis, dermatomyositis, Ehlers-Danlos syndrome, epidermolysis bullosa, erythromelalgia, genetic skin disorders, graft-versus-host disease, granuloma annulare, graves' disease, hair diseases, hair loss, hemangioma, hidradenitis suppurativa, hypereosinophilic syndrome, hyperhidrosis, itchy skin (pruritus), keloids, Klippel-Trenaunay syndrome, lichen planus, lip cancer, lymphoma, melanoma, merkel cell carcinoma, moles, morphea, mucous membrane diseases, nail diseases, nephrogenic systemic fibrosis, neurofibromatosis, nonmelanoma skin cancer, oral lichen planus, panniculitis, pemphigus, pigmentation disorders, polymorphous light eruption, primary biliary cholangitis, psoriasis, pyoderma gangrenosum, rosacea, scleroderma, skin cancer, skin infections, spider veins, squamous cell carcinoma of the skin, Stevens-Johnson syndrome, subcutaneous fat diseases, sun allergy, varicose veins, vascular anomalies, vasculitis, vitiligo, vulvar skin disorders, and wrinkles.

In certain embodiments, the disease is ophthalmological. In certain embodiments, the disease is selected from the group consisting of age-related macular degeneration, amblyopia (lazy eye), anophthalmia and microphthalmia, astigmatism, Behçet's disease, Bietti's crystalline dystrophy, blepharitis, blepharospasm, cataracts, cerebral visual impairment (CVI), coloboma, color blindness, convergence insufficiency, corneal conditions, diabetic retinopathy, dry eye, farsightedness (hyperopia), floaters, glaucoma, idiopathic intracranial hypertension, low vision, macular edema, macular hole, macular pucker, nearsightedness (myopia), ocular histoplasmosis syndrome (OHS), pink eye, presbyopia, rare diseases, refractive errors, retinal detachment, retinitis pigmentosa, retinoblastoma, retinopathy of prematurity, Stargardt disease, Usher syndrome, uveitis, and vitreous detachment.

In certain embodiments, provided herein are methods for the treatment that include the administration of an effective amount of a compound provided herein, or a pharmaceutically acceptable salt thereof. In certain embodiments, the methods encompass the step of administering to the subject in need thereof an amount of a compound described herein effective for the treatment of disease or disorder in combination with a second agent effective for the treatment or prevention of the disease or disorder. In certain embodiments, the compound is in the form of a pharmaceutical composition, or dosage form, as described elsewhere herein.

In certain embodiments, the subject is a treatment naïve subject. In further embodiments, the subject has previously received therapy. For instance, in certain embodiments, the subject has not responded to a single agent treatment regimen.

In certain embodiments, the subject is a subject that discontinued some other therapy because of one or more adverse events associated with the other therapy. In certain embodiments, the subject has received some other therapy and discontinued that therapy prior to administration of a method provided herein. In further embodiments, the subject has received therapy and continues to receive that therapy along with administration of a compound provided herein. The compounds described herein can be co-administered with other therapy for treatment of the disease or disorder according to the judgment of one of skill in the art. In certain embodiments, the methods or compositions provided herein can be co-administered with a reduced dose of the other therapy for the treatment of the disease or disorder.

Diagnostic Applications

In some embodiments, the compounds provided herein are used in diagnostic applications. These applications may be useful, for example, in making a diagnosis and/or prognosis for a disease or disorder, such as a proliferative, dermatological, or ophthalmological disease or disorder.

In some diagnostic and prognostic applications or embodiments, the compound may be labeled with a detectable moiety. Suitable detectable moieties include, but are not limited to, radioisotopes, fluorescent labels, and enzyme-substrate labels. In another embodiment, the compound need not be labeled, and the presence of the compound can be detected using a labeled antibody, or antigen binding fragment thereof which specifically binds to the compound.

Kits

In some embodiments, a compound provided herein is provided in the form of a kit (i.e., a packaged combination of reagents in predetermined amounts with instructions for performing a procedure). In some embodiments, the procedure is a diagnostic assay. In certain embodiments, the procedure is a therapeutic procedure.

In some embodiments, the kit further comprises a solvent for the reconstitution of the compound. In some embodiments, the compound is provided in the form of a pharmaceutical composition.

In some embodiments, the kits can include a compound or composition provided herein, an optional second agent or composition, and instructions providing information to a health care provider regarding usage for treating the disorder. Instructions may be provided in printed form or in the form of an electronic medium such as a floppy disc, CD, or DVD, or in the form of a website address where such instructions may be obtained. A unit dose of a compound or a composition provided herein, or a second agent or composition, can include a dosage such that when administered to a subject, a therapeutically or prophylactically effective plasma level of the compound or composition can be maintained in the subject for at least one day. In some embodiments, a compound or composition can be included as a sterile aqueous pharmaceutical composition or dry powder (e.g., lyophilized) composition.

In some embodiments, suitable packaging is provided. As used herein, "packaging" includes a solid matrix, or material customarily used in a system, and is capable of holding within fixed limits a compound provided herein and/or a second agent suitable for administration to a subject. Such materials include, glass and plastic (e.g., polyethylene, polypropylene, and polycarbonate) bottles, vials, paper, plastic, plastic-foil laminated envelopes, and the like. If e-beam sterilization techniques are employed, the packaging should have sufficiently low density to permit sterilization of the contents.

Preparation and Synthetic Procedures

In some embodiments, the compounds described herein are prepared as outlined in Scheme 1. The synthesis of the compounds in this application is not limited to these general reaction schemes illustrated here. For detailed synthesis of each individual compound, please check the Examples section.

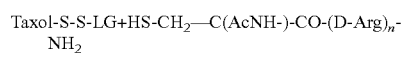

Scheme 1

Scheme 1. Compounds of Formula I or II can be prepared by reaction of a thio-peptide, for instance 4-mercaptobutanoate-$(D-Arg)_n$-$NH_2$, with a dithio-Taxol derivative. In Scheme 1, LG is a leaving group and n is an integer from 1-20, for instance 8. Exemplary reaction conditions are provided in the Examples below.

EXAMPLES

Preparation of the Compounds

The compounds used in the reactions described herein are made according to organic synthesis techniques known to those skilled in this art, starting from commercially available chemicals, and/or from compounds described in the chemical literature. "Commercially available chemicals" are obtained from standard commercial sources such as Acros Organics (Pittsburgh, Pa.), Advanced ChemBlocks, Inc (Burlingame, Calif.), Aldrich Chemical (Milwaukee, Wis., including Sigma Chemical and Fluka), AK Scientific (Union City, Calif.), AstaTech, Inc. (Bristol, Pa.), Aurum Pharmatech LLC (Franklin Park, N.J.), Combi-Blocks, Inc. (San Diego, Calif.), Enamine (Monmouth Jct., N.J.), Fisher Scientific Co. (Pittsburgh, Pa.), Frontier Scientific (Logan, Utah), TCI America (Portland, Oreg.), and VWR (Radnor, Pa.). Specific and analogous reactants are optionally identified through the indices of known chemicals prepared by the Chemical Abstract Service of the American Chemical Society, which are available in most public and university libraries, as well as through on-line databases.

Suitable reference books that detail the synthesis of reactants useful in the preparation of compounds described herein, or provide references to articles that describe their preparation, include for example, "Synthetic Organic Chemistry", John Wiley & Sons, Inc., New York; S. R. Sandler et al., "Organic Functional Group Preparations," 2nd Ed., Academic Press, New York, 1983; "T. L. Gilchrist, "Heterocyclic Chemistry", 2nd Ed., John Wiley & Sons, New York, 1992; and J. March, "Advanced Organic Chemistry: Reactions, Mechanisms and Structure", 4th Ed., Wiley-Interscience, New York, 1992; R. C. Larock "Comprehensive Organic Transformations: A Guide to Functional Group Preparations" 2nd Edition (1999) Wiley-VCH, ISBN: 0-471-19031-4; "Organic Reactions" (1942-2000) John Wiley & Sons, in over 55 volumes; and "Chemistry of Functional Groups" John Wiley & Sons, in 73 volumes. Some compounds require the application of protecting groups. The need for such protection is within the skill in the art. For a general description of protecting groups and their use, see T. W. Greene, P. G. M. Nuts, and Protective Groups in Organic Synthesis, John Wiley & Sons, New York, 1999.

Analytical Methods and Instrumentation

The compounds prepared by the reactions described herein are characterized according to analysis techniques known to those skilled in this art. High-performance liquid chromatography (HPLC) is a technique in analytical chemistry used to separate, identify, and quantify each component in a mixture. Reverse phase high-performance liquid chromatography (RP-HPLC) is an HPLC technique that uses a hydrophobic stationary phase. Preparative-scale high performance liquid chromatography (HPLC) (prep-HPLC) is a separation technique to produce a quantity of pure compound. Liquid chromatography-mass spectrometry (LC-MS) is an analytical chemistry technique that combines the physical separation capabilities of high-performance liquid chromatography (HPLC) with the mass analysis capabilities of mass spectrometry (MS).

Suitable reference books that detail the analysis techniques described herein include for example, Lloyd R. Snyder et al., "Practical HPLC Method Development" 2nd Ed., Wiley-Interscience; New York, 1997; Michael W. Dong, "HPLC and UHPLC for Practicing Scientists" 2nd Ed., Wiley; 2019; Marvin C. McMaster, "LC/MS: A Practical User's Guide", Wiley-Interscience, 2005 and Stavros Kromidas, "The HPLC-MS Handbook for Practitioners" 1st Ed., Wiley-VCH, 2017.

Abbreviations used in the examples include:

| Abbreviation | Name |
|---|---|
| ACN | acetonitrile |
| Ac | acetyl |
| DIPEA | diisopropylethylamine |
| DMF | N,N-dimethylformamide |
| EDT | ethanedithiol |
| Fmoc | fluorenylmethoxycarbonyl |
| g | grams |
| h | hours |
| $H_2O$ | water |
| HCl | hydrochloric acid |
| HPLC | high performance liquid chromatography |
| LCMS | liquid chromatography mass spectrometry |
| mmol | milimole |
| MBHA | 4-methylbenzhydrylamine |
| MS | mass spectrometry |
| RP-HPLC | reverse phase high performance liquid chromatography |
| TFA | trifluoracetic acid |

Unless otherwise noted, reagents and solvents were used as received from commercial suppliers. Anhydrous solvents and oven-dried glassware were used for synthetic transformations sensitive to moisture and/or oxygen. Reaction times and yields were not optimized. Example numbers and compound numbers are the same.

Example 1. Ac-L-Cysteine (paclitaxel-4-mercaptobutanoate)-D-Arginine$_8$-NH$_2$ (1)

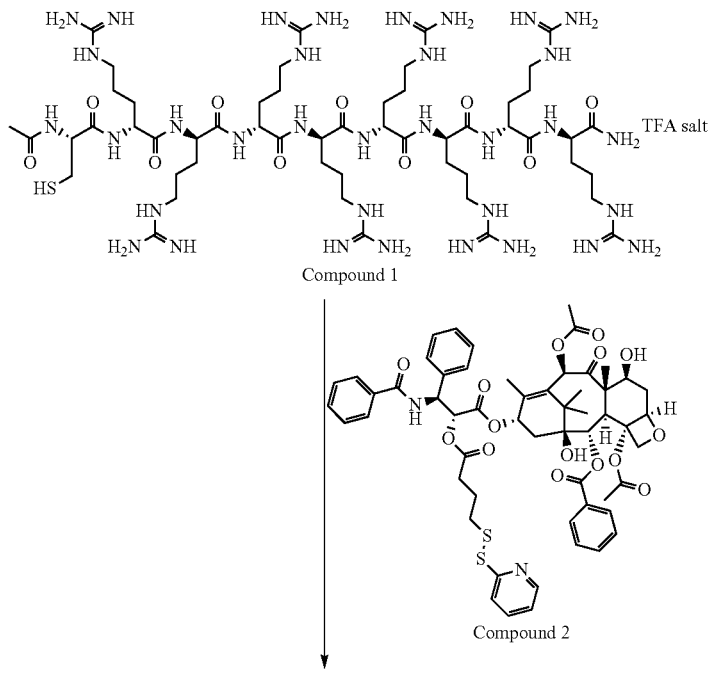

Compound 1

Compound 2

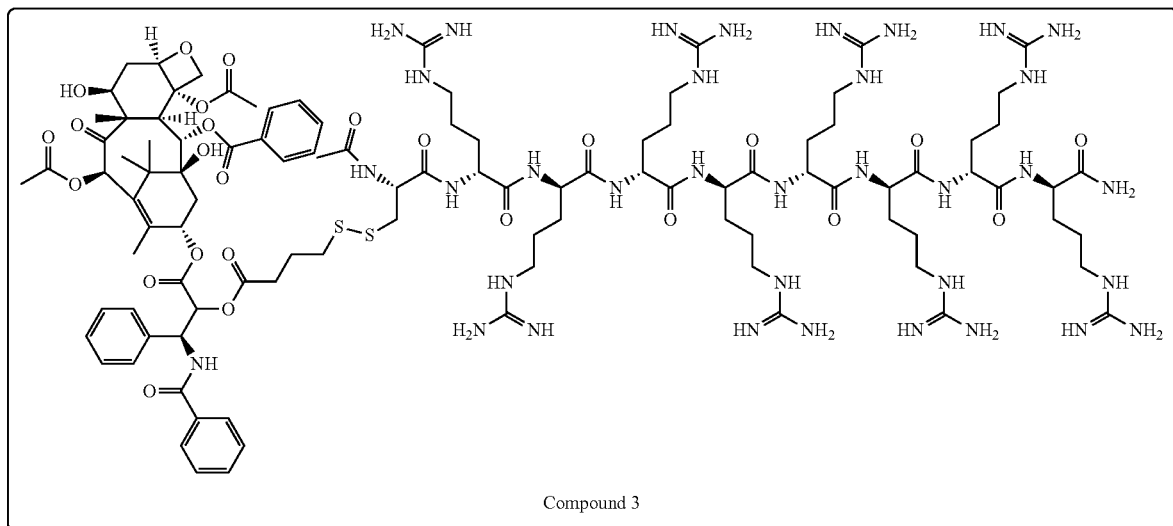

Compound 3

Step A. Ac-L-Cysteine-D-Arginine$_8$-NH$_2$ (1)

Rink Amide MBHA Resin (2.0 mmol. 0.383 mmol/g, 5.23 g) was used as solid support to prepare Compound 1 by Fmoc strategy on a peptide synthesizer. After the desired sequences reached completion, 14.4 g of peptide resin was obtained, which was then treated with a TFA cocktail (TFA: thioanisole:phenol:EDT:H$_2$O=87.5:5:2.5:2.5:2.5) for 3 h to cleave peptides from the solid support and remove all side-chain protecting groups. The resulting suspension was filtered to remove solid resin and the filtrate containing peptides was precipitated into 10 times of cold ether. The precipitates were collected by centrifugation, washed with cold ether twice, and dried under vacuum to give 1.74 g of crude compound. The crude Compound 1 was purified by prep-HPLC with TFA buffer (Buffer A: 0.1% TFA in H$_2$O; Buffer B: 0.1% TFA in 80% ACN+20% H$_2$O) to give 1.04 g pure Compound 1, Ac-L-Cysteine-D-Arginine8-NH$_2$, as a TFA salt (90% purity, 59.6% yield).

Step B. Ac-L-Cysteine (paclitaxel-4-mercaptobutanoate)-D-Arginine$_8$-NH$_2$ (3)

To a solution of Compound 1 (1.3 eq, 1.00 g, 0.430 mmol) and Compound 2 (1 eq, 0.353 g, 0.331 mmol; Rodrigues et al., 1995, Chem Biol 2:223-227; Dubikovskaya et al., 2008, Proc Natl Acad Sci. 105:12128-12133) in DMF (70 ml) was added DIPEA (5.2 eq, 0.30 ml, 1.72 mmol) while stirring. The reaction mixture was stirred at room temperature overnight, monitored by HPLC and MS until Compound 1 was fully consumed. After quenching with H$_2$O, the reaction mixture was stirred for additional 2 h. The crude product of Compound 3 was diluted with ACN/H$_2$O followed by loading onto RP-HPLC for purification with TFA buffer (Buffer A: 0.1% TFA in H$_2$O; Buffer B: 0.1% TFA in 80% ACN+20% H$_2$O). The fractions contained the desired peptide were collected and lyophilized to give 543 mg of Compound 3, Ac-L-Cysteine (Paclitaxel-4-mercaptobutanoate)-D-Arginine$_8$-NH$_2$, as an off-white powder (98.3% purity). The yield after conjugation and purification is 69.5% based on Compound 2. LCMS: Calc: 2365.7; Found: 2365.

Example 2. Ac-D-Cysteine (paclitaxel-4-mercaptobutanoate)-D-Arginine$_8$-NH$_2$ (5)

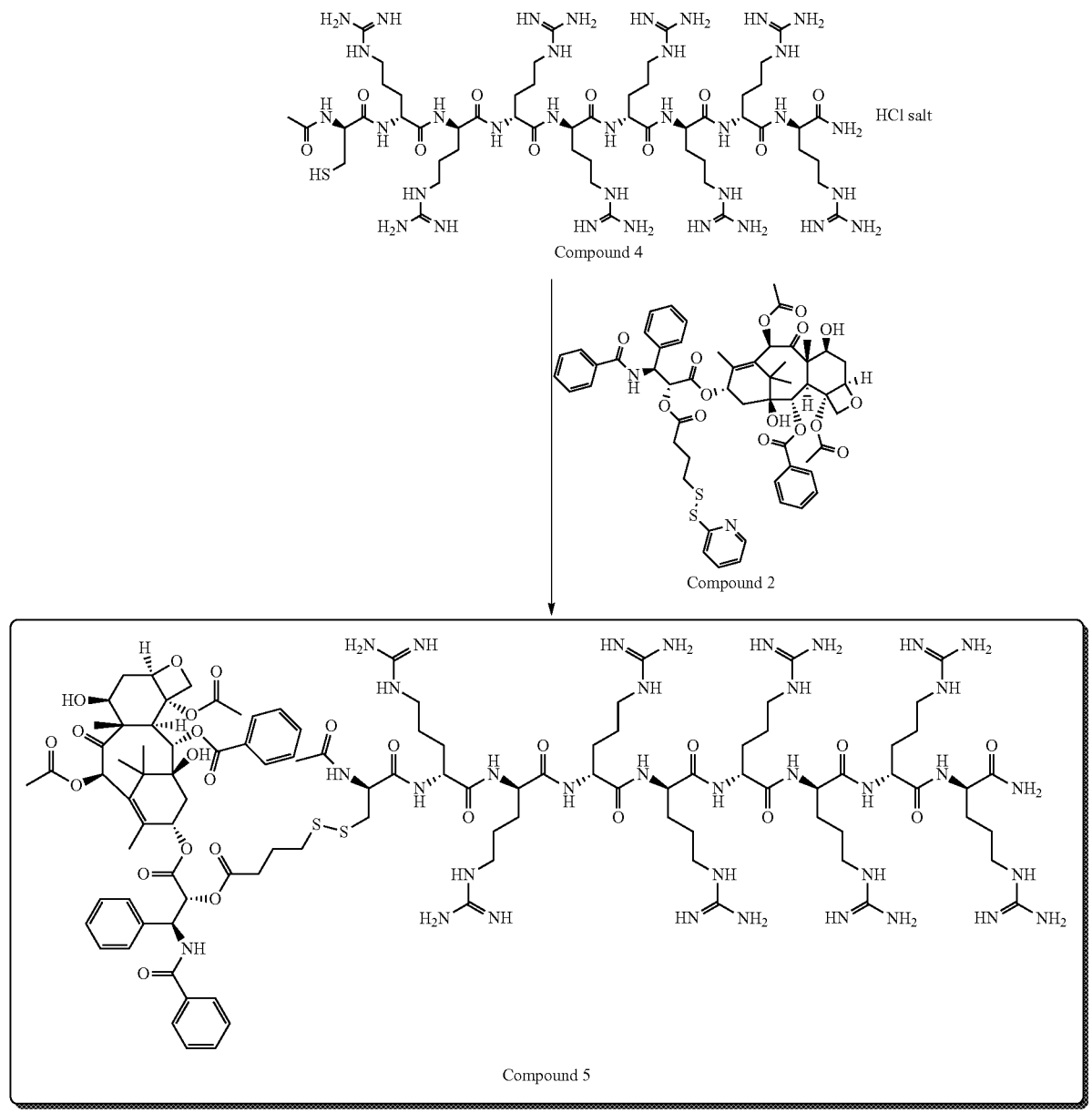

Compound 4

Compound 2

Compound 5

Step A. Ac-D-Cysteine-D-Arginine$_8$-NH$_2$ (4)

Rink Amide MBHA Resin (10.0 mmol. 0.316 mmol/g, 32.7 g) was used as solid support to prepare Compound 4 by Fmoc strategy on a peptide synthesizer. After the desired sequences reached completion, 71.3 g of peptide resin was obtained, which was then treated with a TFA cocktail (TFA:thioanisole:phenol:EDT:H$_2$O=87.5:5:2.5:2.5:2.5) for 3 h to cleave peptides from the solid support and remove all side-chain protecting groups. The resulting suspension was filtered to remove solid resin and the filtrate containing peptides was precipitated into cold ether. The precipitates were collected by centrifugation, washed with cold ether twice, and dried under vacuum to give 13.4 g of crude Compound 4. The crude Compound 4 was purified by prep-HPLC with TFA buffer (Buffer A: 0.1% TFA in H$_2$O; Buffer B: 0.1% TFA in 80% ACN+20% H$_2$O) followed by ion exchange to HCl salt using HCl buffer (Buffer A: 0.05% HCl in H$_2$O; Buffer B: 0.05% HCl in 80% ACN+20% H$_2$O) to give 4.49 g pure Compound 4, Ac-D-Cysteine-D-Arginine8-NH$_2$, as a HCl salt (95% purity, 33.4% yield).

Step B. Ac-D-Cysteine (paclitaxel-4-mercaptobutanoate)-D-Arginine$_8$-NH$_2$ (5)

To a solution of Compound 4 (1.3 eq, 0.930 g, 0.546 mmol) and Compound 2 (1 eq, 0.447 g, 0.420 mmol) in DMF (50 ml) was added DIPEA (5.2 eq, 0.382 ml, 2.19 mmol) while stirring. The reaction mixture was stirred at room temperature overnight, monitored by HPLC and MS until Compound 4 was fully consumed. After quenching with H$_2$O, the reaction mixture was stirred for additional 2 h. The crude product of Compound 5 was diluted with ACN/H$_2$O followed by loading onto RP-HPLC with TFA buffer (Buffer A: 0.1% TFA in H$_2$O; Buffer B: 0.1% TFA in 80% ACN+20% H$_2$O) for purification. The fractions contained the desired peptide were collected and lyophilized to give 818 mg of Compound 5, Ac-D-Cysteine (Paclitaxel-4-mercaptobutanoate)-D-Arginine8-NH$_2$, as an off-white powder (97.9% purity). The yield after conjugation and purification is 82% based on Compound 2. LCMS: Calc: 2365.7; Found: 2365.5.

Biological Example 1

Cytotoxicity Assay—CCK8 Cancer Cells

The CCK-8 assay was applied to study the cytotoxicity of the peptide drug conjugates and their inhibition of proliferation of cancer cells. First, 2~10×10$^3$ cells (depending on the rate of growth of different cell lines) with 100 μL, DMEM media were seeded in normal culture medium into each well of a 96-well plate. The cells were then cultured overnight at 37° C. with 4~5% CO$_2$. Different doses (4000, 2000, 1000, 500 nM for Hep3B, Hep G2 and MCF7/MBA-MD-231; 1000, 333.3, 100.0, 33.33, 3.333, 1.000, 0.333 nM for MCF7/ADR, 22Rv1, CNE1, HCT116, DLD-1) of Taxol and peptide drugs were added. After 48~72 hour incubation, CCK-8 solution was added to each well. The cells were then incubated at 37° C. for 4 hours. The optical density was measured at 450/650 nm using a multiscan spectrometer (PerkinElmer's EnSpire Multilabel Plate Reader). The optical density is linearly proportional to the number of living cells in the sample:

$$\text{Cell Viability}(\%) = \frac{OD_{compound} - OD_{background}}{OD_{DMSO} - OD_{background}} \times 100$$

The plate layout for MCF7/ADR, 22Rv1, CNE1, HCT116, DLD-1 cell lines is shown below.

liver cancer Hep 3B cells 11.5% at a dose of 4 μM, while Compound 5 (D-cysteine linker) had anti-proliferation 23.2%. Compound 3 (L-cysteine linker) provided substantially higher efficacy compared to Compound 5 (D-cysteine linker) and Taxol with 36.0% cancer cells inhibition (Table 1A).

TABLE 1A

Inhibition of Liver Cancer Hep 3B Cells at 4 μM

| Compound | Anti-proliferation % |
|---|---|
| Taxol | 11.5 |
| Compound 5 (D-cysteine linker) | 23.2 |
| Compound 3 (L-cysteine linker) | 36.0 |

Figure 2A:
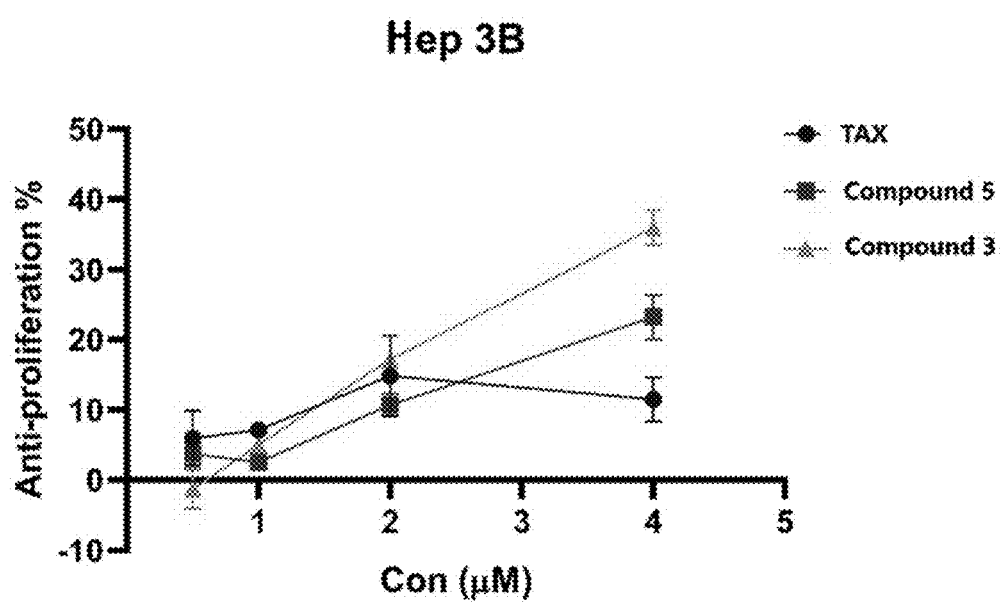
FIG. 2A provides anti-proliferation cell kill percent versus concentration for TAX (Taxol), Compound 5, and Compound 3 in Hep 3B cells as described in Biological Example 1.
Figure 2B:
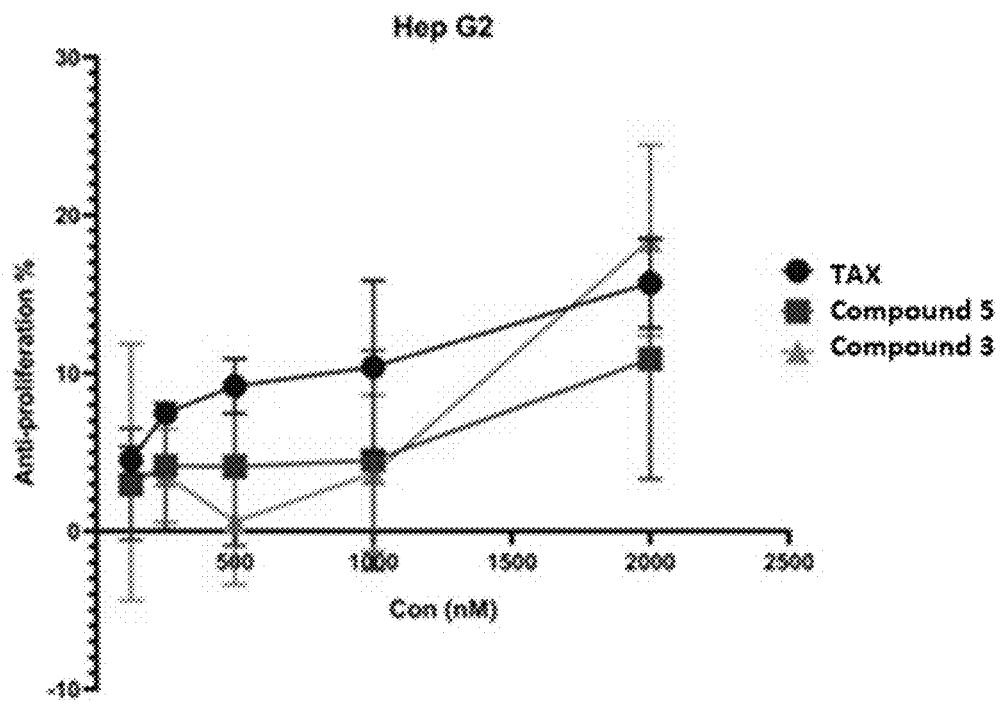
FIG. 2B provides anti-proliferation cell kill percent versus concentration for TAX (Taxol), Compound 5, and Compound 3 in Hep G2 cells as described in Biological Example 1.
Figure 2C:
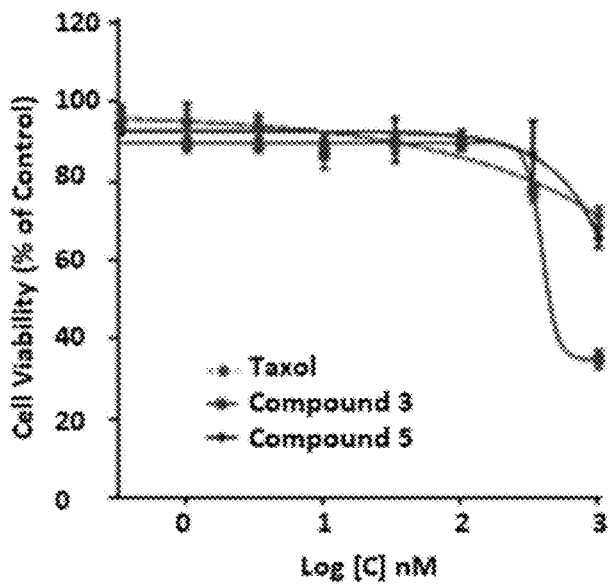
FIG. 2C provides anti-proliferation cell kill percent versus concentration for Taxol, Compound 5, and Compound 3 in MCF7/ADR cells as described in Biological Example 1.
Figure 2D:
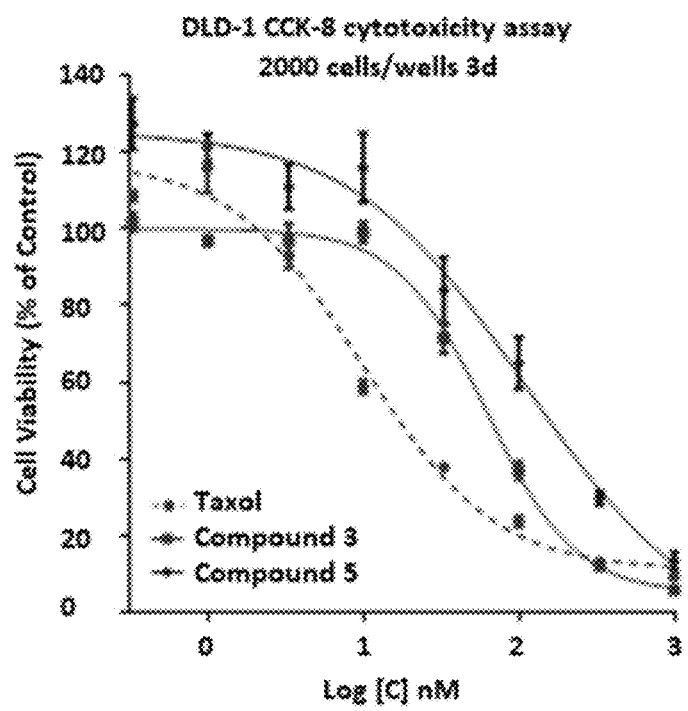
FIG. 2D provides anti-proliferation cell kill percent versus concentration for Taxol, Compound 5, and Compound 3 in DLD-1 cells as described in Biological Example 1.
Figure 2E:
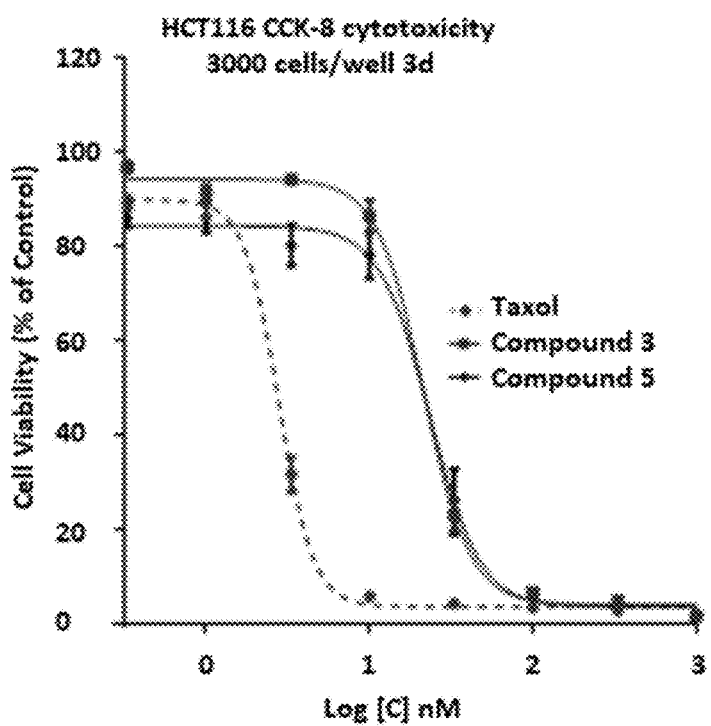
FIG. 2E provides anti-proliferation cell kill percent versus concentration for Taxol, Compound 5, and Compound 3 in HCT116 cells as described in Biological Example 1.
Figure 2F:
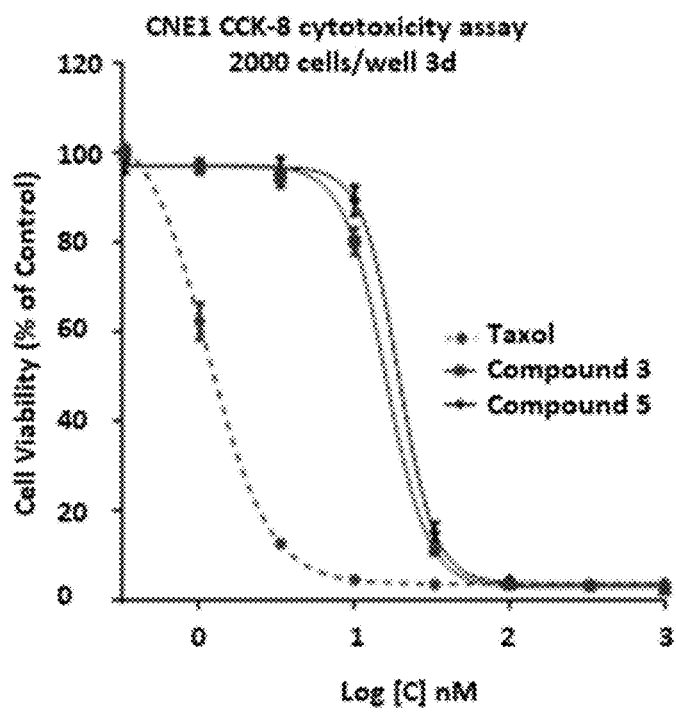
FIG. 2F provides anti-proliferation cell kill percent versus concentration for Taxol, Compound 5, and Compound 3 in CNE1 cells as described in Biological Example 1.
Figure 2G:
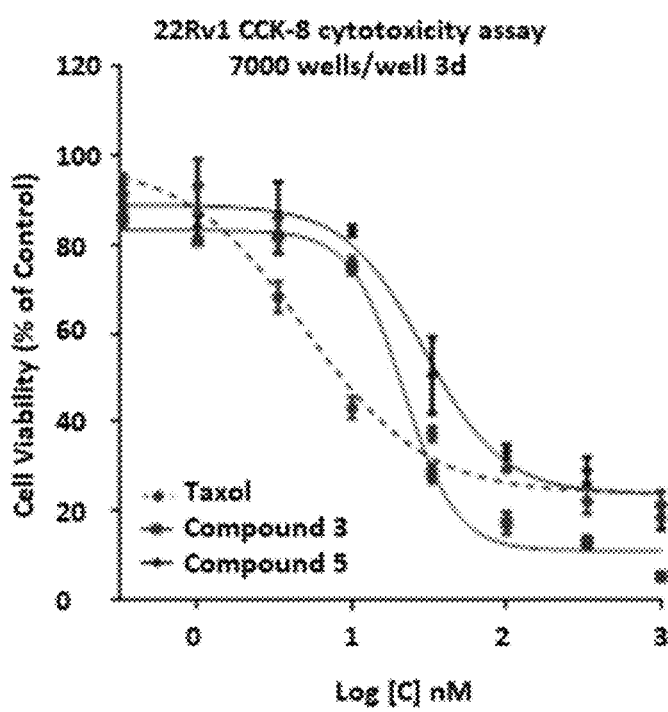
FIG. 2G provides anti-proliferation cell kill percent versus concentration for Taxol, Compound 5, and Compound 3 in 22Rv1 cells as described in Biological Example 1.

The inhibition of Compound 5 and Compound 3 in Hep G2 cells are shown in FIG. 2B. The anti-proliferation effect of Compound 3 was greater than the anti-proliferation effect of Taxol and Compound 5 at a concentration of 2000 nM.

The results from the proliferation experiments in MCF7/ADR, 22Rv1, CNE1, HCT116, DLD-1 are shown in Table 1B and FIGS. 2C-2G. Compound 3 exhibited a lower IC$_{50}$ value compared to Compound 5 in all cell lines tested. Importantly, Compound 3 exhibited an IC$_{50}$ value of 437.5 nM against the multidrug-resistant breast cancer (MCF7/ADR) cell line, while both Compound 5 and Taxol exhibited an IC$_{50}$ of >1000 nM.

TABLE 1B

Inhibition of MCF7/ADR, 22Rv1, CNE1, HCT116, DLD-1 Cells Cell line

| | Taxol IC$_{50}$ nM | Compound 3 IC$_{50}$ nM | Compound 5 IC$_{50}$ nM |
|---|---|---|---|
| MCF7/ADR multidrug-resistant breast cancer cell | >1000 | 437.5 | >1000 |
| 22Rv1 human prostate carcinoma epithelial cell line | 4.949 | 21.56 | 29.32 |

| | | | Cpds | | | | | | | |
|---|---|---|---|---|---|---|---|---|---|---|
| | | | Taxol | | | Compound 3 | | | Compound 5 | |
| Conc. | 1 | 2 | 3 | 4 | 5 | 6 | 7 | 8 | 9 | 10 | 11 |
| A | background | 1‰ | 1000 nM | | | 1000 nM | | | 1000 nM | | |
| B | | DMSO | 333.3 nM | | | 333.3 nM | | | 333.3 nM | | |
| C | | | 100.0 nM | | | 100.0 nM | | | 100.0 nM | | |
| D | | | 33.33 nM | | | 33.33 nM | | | 33.33 nM | | |
| E | | | 10.00 nM | | | 10.00 nM | | | 10.00 nM | | |
| F | | | 3.333 nM | | | 3.333 nM | | | 3.333 nM | | |
| G | | | 1.000 nM | | | 1.000 nM | | | 1.000 nM | | |
| H | | | 0.333 nM | | | 0.333 nM | | | 0.333 nM | | |

It was found that there was a good correlation between anti-proliferation and concentration for peptide drug conjugates Compound 3 (L-cysteine linker) and Compound 5 (D-cystine linker) was observed in the MCF7/MBA-MD-231 and liver cancer Hep 3B cells. The inhibition change with concentration increase for Taxol was not observed. A significantly strong cancer cell inhibition was observed at high conjugate concentrations. Both peptide drug conjugates provided better cancer cell killing properties than Taxol. Compound 3 was substantially superior to cancer cell inhibition compared to Compound 5 at all tested concentrations for both breast cancer MCF7/MBA-MD-231 (FIG. 1) and liver cancer Hep 3B cells (FIG. 2A). Taxol only inhibited TABLE 1B-continued Inhibition of MCF7/ADR, 22Rv1, CNE1, HCT116, DLD-1 Cells Cell line

| | Taxol IC$_{50}$ nM | Compound 3 IC$_{50}$ nM | Compound 5 IC$_{50}$ nM |
|---|---|---|---|
| CNE1 nasopharyngeal carcinoma cell line | 1.122 | 15.95 | 19.29 |
| HCT116 human colorectal carcinoma cell | 2.788 | 21.48 | 23.5 |

TABLE 1B-continued

Inhibition of MCF7/ADR, 22Rv1, CNE1, HCT116, DLD-1 Cells Cell line

| | Taxol IC$_{50}$ nM | Compound 3 IC$_{50}$ nM | Compound 5 IC$_{50}$ nM |
|---|---|---|---|
| DLD-1 colorectal adenocarcinoma cell line isolated from the large intestine of a colon adenocarcinoma patient | 9.979 | 62.04 | 110.3 |

Biological Example 2

Stability in Buffer

Working solutions of Compound 5 (1 mM of) and Compound 3 (1 mM) were prepared. Buffer solution (199 μL) was prepared and divided into fourteen incubation tubes. The tubes were then pre-warmed at 37° C. for 15 minutes. The 1 mM Compound 5 working solution was added to seven incubation tubes (1 μL each) for a final concentration of 5 μM and the 1 mM Compound 3 working solution was added to seven incubation tubes (1 μL each) for a final concentration of 5 μM. For Compound 5, the final concentration of organic solvents was 0.5%. Each samples was incubated at 37° C. for 0, 4, 8, 24, 48, 72, or 120 hours. The assay was performed in duplicate. After incubation for 0, 4, 8, 24, 48, 72 or 120 hours, reactions were quenched by the addition of 1000 μL methanol (pre-cool treatment under 4° C.) with 2% FA containing internal standards. All samples were vortexed for 10 minutes. 150 μL of the supernatant from each sample was transferred to a new plate. 150 μL of pure water was added to each sample for analysis by LC-MS/MS (cooler temperature: 15° C.). All calculations were carried out using Microsoft Excel. Peak area ratios were determined from extracted ion chromatograms. Percent compounds remaining at each time point were calculated by the following equation:

Remaining Percentage$_{t\ min}$(%)=(Peak Area Ratio$_{t\ min}$/Peak Area Ratio$_{0\ min}$)×100 wherein

Peak Area Ratio$_{t\ min}$ is peak area ratio of test compounds at t min; and

Peak Area Ratio$_{0\ min}$ is peak area ratio of test compounds at zero time point.

The slope value, k, was determined by linear regression of the natural logarithm of the remaining percentage of the parent drug vs. incubation time curve.

The in vitro half-life (in vitro $t_{1/2}$) was determined from the slope value:

in vitro $t_{1/2}$=(0.693/k)

Appearance of Taxol concentration (nM)=Peak Area Ratio $t$ min/Peak Area Ratio(Taxol: 5 μM)× 5000%

Appearance of Taxol=Peak Area Ratio min/Peak Area Ratio(Taxol: 5 μM)×100

The rules for data processing are shown in Table 2.

TABLE 2

Processing Rules for Data Processing

| Remaining % | Processing Rules |
|---|---|
| ≥80% at 120 hour | If T-test with p<0.05 is obtained, report the calculated $t_{1/2}$ value. If T-test with p<0.05 is not obtained, then report "∞" for $t_{1/2}$ value when all the other data points fall in the range of 80%~120% (one data point within the range of 70%~130% is accepted), otherwise the experiment should be repeated |
| <80% at 120 hour | Always remove from the calculation all points with <10% left of 0 min sample, but leave at least 2 points. If T-test with p<0.05 is obtained, report the calculated $t_{1/2}$ value. If T-test with p<0.05 is not obtained, the experiment must be repeated |

The stability of Compound 5 and Compound 3 in aqueous buffered solution was studied at different pH and the results are shown in Table 3. Unexpectedly, the half-life of Compound 3 was longer in all pH tested, with the longest half-life in a pH 5.5 solution. The numbers represent the average value of two parallel experiments. The longer half-life of Compound 3, substituted with the L-Cys-D-arg8, in aqueous buffered solutions is an unexpected finding of better stability against the hydrolysis of the linker. Compound 5 with a D-Cys-D-arg8 was predicted to be more stable than Compound 3 because the unnatural amino acid presence is known to be more resistant to protease cleavage.

TABLE 3

Stability of Compound 3 Compared to Compound 5 in Buffer Solutions of Varying pH

| | Mean T $_{1/2}$ (hour) | | Percent |
|---|---|---|---|
| | Compound 5 | Compound 3 | Increase |
| pH 5.5 | 117.45 | 124.56 | 6.05% |
| pH 6.0 | 93.50 | 99.45 | 6.36% |
| pH 6.5 | 85.44 | 92.28 | 8.01% |
| pH 7.4 | 49.38 | 54.65 | 10.67% |

Biological Example 3

Stability in Plasma

Working solutions of test compounds were prepared in PBS (pH 7.4). Propantheline was used as positive control for human, monkey, dog and mouse plasma in the assay. Mevinolin was used as positive control for rat plasma in this assay. 1 mM propantheline working solution was prepared in acetonitrile. 1 mM mevinolin working solution was prepared in DMSO. Incubation buffer of 475 μL plasma for each cell was added into the incubation plate and pre-warmed at 37° C. for 15 minutes. After the pre-incubation, 25 μL of working solution (test compounds or control compounds) was spiked to plasma. For Compound 5 and Compound 3, the final concentration of organic concentration was 0%. For Taxol, the final concentration of organic solvents was 0.25%. The assay was performed in duplicate. The reaction samples were incubated at 37° C. Aliquots of 50 μL were taken from the reaction samples at 0, 0.25, 0.5, 1, 2, 4, 6, 8 and 24 hours. The reactions were stopped by the addition of 450 μL of ice-cold quench solution (methanol with 2% FA containing internal standards). All samples were vortexed for 10 minutes, following by centrifugation at 3,220 g for 30 minutes to precipitate proteins. 100 μL of the supernatant from each well was transferred to a new plate. The supernatant was diluted with ultrapure water. Samples were analyzed by LC-MS/MS. All calculations were carried out using Microsoft Excel. Peak area ratios were determined from extracted ion chromatograms. Percent compounds remaining at each time point were calculated by the following equation:

Remaining Percentage$_{t\ min}$(%)=Peak Area Ratio$_{t\ min}$/Peak Area Ratio$_{0\ min}$×100 wherein

Peak Area Ratio$_{t\ min}$ is peak area ratio of control and test compounds at t min; and Peak Area Ratio$_{0\ min}$ is peak area ratio of control and test compounds at zero time point.

The slope value, k, was determined by linear regression of the natural logarithm of the remaining percentage of the parent drug vs. incubation time curve.

The in vitro half-life (in vitro $t_{1/2}$) was determined from the slope value:

in vitro $t_{1/2}$=(0.693/k)

The rules for data processing are shown in Table 4.

TABLE 4

Processing Rules for Data Processing

| Remaining % | Processing Rules |
|---|---|
| ≥80% at 24 h | If T-test with p<0.05 is obtained, report the calculated $t_{1/2}$ value<br>If T-test with p<0.05 is not obtained, then report "∞" for $t_{1/2}$ value when all the other data points fall in the range of 80%~120% (one data point within the range of 70%~130% is accepted), otherwise the experiment should be repeated |
| <80% at 24 h | Always remove from the calculation all points with <10% left of 0 min sample, but leave at least 2 points<br>If T-test with p<0.05 is obtained, report the calculated $t_{1/2}$ value<br>If T-test with p<0.05 is not obtained, the experiment must be repeated |

The results are shown in Table 5. Compound 3 showed a longer half-life than Compound 5 in human, dog, rat and mouse plasma. Although the peptide component of Compound 5 consists of only unnatural amino acids, which are known to be resistant to natural protease in animals, Compound 3 was surprisingly more stable than Compound 5. The longer half-life in plasma in different species of Compound 3 suggests that Compound 3 could be more stable than Compound 5 in vivo.

TABLE 5

Stability of Compound 3 Compared to Compound 5 in Plasma

| | Mean T$_{1/2}$ | | Percent |
|---|---|---|---|
| | Compound 5 | Compound 3 | Increase |
| Human | 1.03 | 1.22 | 18.45% |
| Dog | 2.76 | 2.79 | 1% |
| Rat | 0.30 | 0.45 | 50% |
| Mouse | 0.79 | 1.06 | 34.18% |

Biological Example 4

In-Life Pharmacokinetics of Compound 3 and Compound 5

General Procedure: A single-dose study was conducted in CD-1 mice. Groups (12 animals in each group) were administered an intraperitoneal (IP) dose of either Taxol (10 mg/kg), Compound 3 (38.4 mg/kg), or Compound 5 (38.4 mg/kg). Serial or terminal plasma samples (n=3 per time-point) were collected from study animals at pre-determined times post-dose. Each mouse was serial bled 2 times (orbital bleeds) and one terminal bleed. The samples were collected in pre-chilled tubes for all steps. Upon completion of the in-life phase, the samples were analyzed using LC-MS/MS.

Assay Procedures: For analysis of analytes in mouse plasma, a 50.0 μL aliquot of each study sample was extracted with protein precipitation using 200 μl of 5% formic acid in methanol. Internal standards were added by adding 25.0 μL methanol containing 250 ng/mL tolbutamide and 1000 ng/mL Taxol-d5.

For Compound 5 and Compound 3 analysis, following centrifugation at 4000 rpm for 10 minutes, 150 μL of the supernatant was transferred to a clean 96 well collection plate for LC-MS/MS analysis.

For Taxol analysis, following centrifugation at 4000 rpm for 10 minutes, 75.0 μL of the supernatant was transferred into a clean 96 well collection plate containing 75.0 μL of deionized water. The plate was then capped and vortexed at 1650 rpm for 3 minutes prior to LC-MS/MS analysis.

Preparation of Standards and Quality Controls: Calibration standards of Compound 3 in mouse plasma were prepared on wet ice in blank mouse plasma at concentrations of 5.00, 10.0, 50.0, 100, 200, 250, 450, and 500 ng/mL. The low quality control ([LQC], 15.0 ng/mL), medium quality control ([MQC], 120 ng/mL) and high quality control ([HQC], 400 ng/mL) were prepared in blank mouse plasma.

Calibration standards of Taxol in mouse plasma were prepared on wet ice in blank mouse plasma at concentrations of 2.50, 5.00, 25.0, 125, 625, 1250, 2250, and 2500 ng/mL. The LQC, (7.50 ng/mL), MQC (120 ng/mL), and HQC (2000 ng/mL) were prepared in blank mouse plasma.

All calibration standard solutions and QC solutions were freshly prepared and discarded after use.

Sample Analyses: Mouse plasma samples were received from the in-life and were stored in a freezer set to −80° C.

Study samples were analyzed in 2 batches. At a minimum, each batch included the following: one set of calibration standards, a matrix blank (blank mouse plasma), a control-zero sample (blank mouse plasma with internal standard), and duplicate QC samples at 3 concentration levels (low, medium, and high) in addition to the study samples. Within each batch, the study samples were bracketed by calibration standards or QC samples.

Data Acquisition and Processing: The LC-MS/MS data acquisition was performed on an Agilent 1290 Infinity II HPLC system coupled with an AB SCIEX API 6500+ mass spectrometer. Chromatograms were integrated using Analyst 1.6.3 software. A weighted (1/x2, x=concentration) linear regression was used to generate the calibration curves and the regression was performed using Analyst 1.6.3 software. The concentration of the analyte in the samples was calculated using the peak area ratios of analyte to internal standard based on the calibration curve.

Data Calculations

The linear formula used to calculate the calibration curves was as follows:

$$y = ax + b$$

wherein y represents the peak area ratio;
a represents the slope of the line;
x represents the concentration; and
b represents the y intercept.

The accuracy (or the degree of closeness of the measured value to its nominal value), expressed as a percentage, was calculated as follows:

% Accuracy=(Measured value)/(Nominal value)×100

The deviation or DEV (of the measured value from its nominal), expressed as a percentage, was calculated as follows:

% DEV=(Measured value−Nominal value)/(Nominal value)×100

The standard deviation (SD) was calculated as follows:

$$SD = \sqrt{\frac{\sum (x - \bar{x})^2}{n - 1}}$$

where, x represents the sample concentration;
$\bar{x}$ represents the mean sample concentration; and
n represents the sample size.

The precision or coefficient of variation (CV), expressed as a percentage, was calculated as follows:

% CV=(Standard deviation)/Mean×100.

Acceptance Criteria: The analytical batches were accepted if the calibration standards and the QC data met the acceptance criteria described below and in SOP BA-018, Bioanalytical Sample Analysis for Non-Regulated Studies.

Calibration Standards: For a calibration standard to be accepted, the back-calculated concentration for each standard had to be 100%±25% of its nominal concentration. For a run to be accepted, a minimum of 67% of standards had to meet these criteria.

Quality Control Samples: For a QC sample to be accepted, its measured concentration had to be 100%±25% of the nominal concentration. For a batch to be accepted, the measured concentrations of at least two-thirds of all QC (LQC, MQC and HQC) samples within the curve range and at least half of the QC samples at each concentration level (low, medium, and high) had to be 100%±25% of their respective nominal concentrations.

The results from the quantitative bioanalysis of Compound 3, Compound 5, and Taxol pharmacokinetics in CD-1 mice are shown in Table 6A and Table 6B. The results are the mean for each group (Compound 3, Compound 5, and Taxol) of mice.

TABLE 6A

PK Results from In-Life Study

| Dosage (mg/kg) | Analyte | $T_{1/2}$ (h) | $C_{max}$ (nm) | $T_{max}$ (h) |
|---|---|---|---|---|
| Compd 3  38.4 | Compd 3 | 0.53 | 88.6 | 0.25 |
|  | Taxol | 21.675 | 320 | 0.67 |
| Compd 5  38.4 | Compd 5 | 1.35 | 993.76 | 0.25 |
|  | Taxol | 16.26 | 217.82 | 1.00 |
| Taxol  10 | Taxol | 2.99 | 1146.97 | 1.00 |

TABLE 6B

PK Results from In-Life Study

| Dosage (mg/kg) | Analyte | $AUC_{0-t}$ (h*nmol/L) | $AUC_{0-inf}$ (h*nmol/L) | $AUMC_{0-t}$ (h*h*nmol/L) | Taxol/Cmpd AUC Ratio |
|---|---|---|---|---|---|
| Cmpd 3  38.4 | Cmpd 3 | 50.585 | 54.595 | 26.304 | NA |
|  | Taxol | 4139.733 | 4387.884 | 72,372.302 | 81.84 |
| Cmpd 5  38.4 | Cmpd 5 | 830.67 | 848.58 | 830.67 | NA |
|  | Taxol | 3274.99 | 3302.94 | 3274.99 | 3.942 |
| Taxol  10 | Taxol | 3987.09 | 4001.92 | 3987.09 | NA |

Compound 3 and Compound 5 have different peptide/linker structures. Compound 3 contains a L-cysteine as the linker-peptide and Compound 5 contains a D-cysteine as the linker-peptide. Compound 5 was expected to be more stable than Compound 3 because Compound is substituted with the unnatural D-cysteine linker-peptide, however, as shown in Table 6A and Table 6B, Compound 3 was unexpectedly more stable.

In the in-life mouse PK study, Compound 5 and Compound 3 behaved differently; for example, different values were observed for the in vivo half-life, $C_{max}$ of the parent compound, the AUC and the AUC ratio. The $T_{1/2}$ of Taxol released from Compound 3 was 33.3% longer than that of Taxol released from Compound 5. The AUC of Taxol released from Compound 3 was also much higher than that released from Compound 5. Further, the $T_{1/2}$ of Compound 3 was 21.675 hours, while the $T_{1/2}$ of Taxol was only 2.99 hours. The AUC ratio of Taxol/Compound 3 was 20 times higher than the AUC ratio of Taxol/Compound 5, reflecting a higher Taxol release efficiency of Compound 3 than Compound 5. Additionally, the AUC of Taxol following administration of Compound 3 was higher than the AUC of Taxol following Taxol administration.

The $C_{max}$ of Compound 5 was over 100-fold higher than that of Compound 3, which could explain why, at least in part, there is acute toxicity and animal death in Compound 5-treated animals.

Biological Example 5

Safety: Animal Body Weight Change after Dosing

Method

Animals: Female athymic nude mice were used in this study. The experimental mice were purchased from Shibefu (Beijing) Biotechnology Co., Ltd. (QC number: SCXK Beijing 2019-0010) and maintained in a High Efficiency Particulate Air Filter (HEPA) filtered environment with cages, food and bedding sterilized by irradiation or autoclaving.

Establishment of peritoneal disseminated metastasis model of human ovarian cancer: Human ovarian cancer (SKOV-3-GFP) cells in logarithmic growth period were digested with 0.25% trypsin, rinsed with phosphate buffer (PBS) twice, centrifuged, and suspended with serum-free RPMI1640 medium. Cell suspension ($6\times10^6$/120 μL/mouse) was injected into the peritoneal cavity of each experimental mouse for the establishment of peritoneal disseminated metastasis model of human ovarian cancer.

Groups, testing articles and treatment protocols: Day 4 after cell inoculation, all mice were subjected to systemic imaging using FluorVivo Model-100 (INDEC biosystems, CA, USA). Mice with a small deviation from average tumor load were enrolled in the study. All animals were randomly allocated to the different study groups, 6 mice in each group. Dosing schedule was Q5D (day 0, 5, 10), dosing volume was 10 μl/g, and administration route was intraperitoneal injection. Each dose of Compound 3 or Compound 5 was 9.6 mg/kg (equimolar to 2.5 mg/kg Taxol) and each dose of Taxol was 10 mg/kg. Taxol working solutions were prepared from 6 mg/mL stock solution, while Compounds were dissolved in PBS (pH 7.4) and filtered through 0.22 μm filter.

Monitoring of the experimental mice: During the period of the study, all experimental mice were checked daily for mortality or signs of morbidity. Images of tumor progression were acquired three times a week during the period of the study with the FluorVivo imaging system, Model 100/Mag (INDEC BioSystems, CA, USA). The body weights of the mice were measured three times a week during the period of the study.

Study endpoint: On Day 21 after administration, animals were euthanized by inhalation of excessive anesthetics. All tumors were exposed for imaging (under the same exposure conditions), after which the tumors were removed and weighed with an electronic balance (Sartorius BS 124 S, Germany). The tumor samples were then stored in formalin solution. All the mice in vehicle group produced ascites that were collected and stored in −80° C. refrigerator.

Statistical methods used in efficacy evaluation: Comparison of body weights and tumor burdens in different groups were analyzed using EXCEL t-test with an α=0.05 (two-sided).

Figure 3:
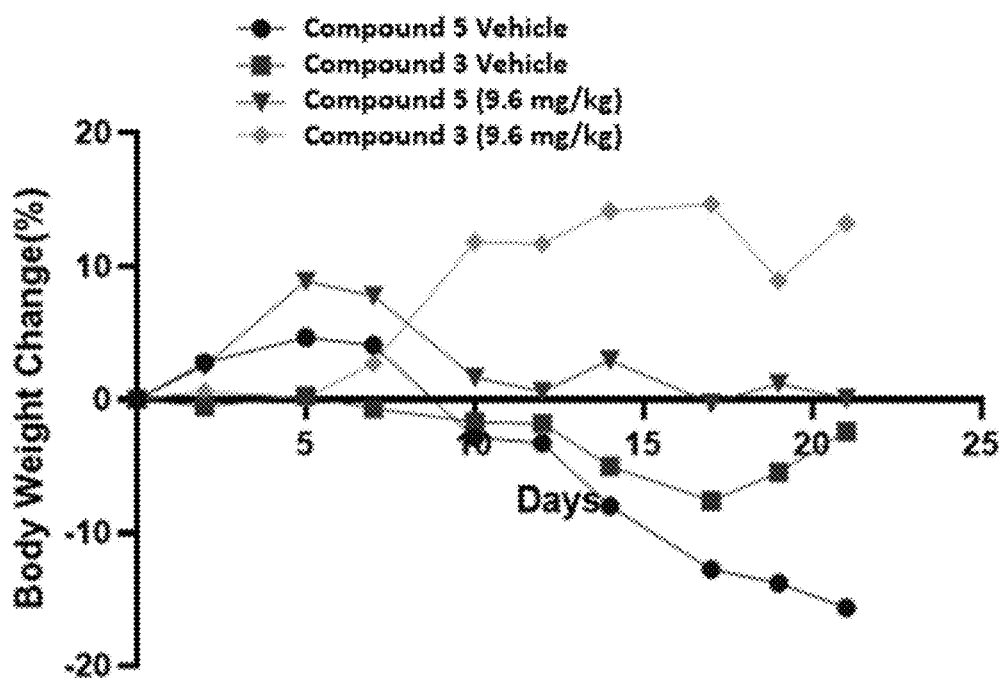
FIG. 3 is a graph of the weight change of mice administered Compound 5 and Compound 3 compared to vehicle over the course of the 21-Day experiment as described in Biological Example 5.

Body weight: The rate of body weight changes are shown in FIG. 3. Table 7A provides the weight change for Compound 3 and Table 7B provides the weight change for Compound 5. Both compounds were separately compared to Taxol as shown in Table 7A and Table 7B. The vehicle was the control.

TABLE 7A

Weight Change of Mice Administered Compound 3

| Groups | Weight on day 0 (MEAN ± SD) | Weight on day 21 (MEAN ± SD) | Weight gain (%) | P value |
| --- | --- | --- | --- | --- |
| Vehicle (PBS) | 15.3 ± 0.8 | 14.9 ± 1.1 | −3 | |
| Taxol (10 mg/kg) | 14.8 ± 0.9 | 17.0 ± 1.5 | 15 | P = 0.02246294 vs Vehicle (PBS) |
| Compd 3 (9.6 mg/kg, equimolar to 2.5 mg/kg Taxol) | 16.3 ± 1.0 | 18.5 ± 1.4 | 13 | P = 0.00054290 vs Vehicle (PBS); P = 0.10288969 vs Taxol (10 mg/kg) |

TABLE 7B

Weight Change of Mice Administered Compound 5

| Groups | Weight on day 0 (MEAN ± SD) | Weight on day 21 (MEAN ± SD) | Weight gain (%) | P value |
| --- | --- | --- | --- | --- |
| Vehicle (PBS) | 17.6 ± 0.8 | 14.8 ± 1.1 | −16 | |
| Taxol (10 mg/kg) | 17.7 ± 0.6 | 19.0 ± 1.2 | 7 | P = 0.000098 vs Vehicle (PBS) |
| Compd 5 (9.6 mg/kg, equimolar to 2.5 mg/kg Taxol) | 16.9 ± 0.6 | 16.9 ± 1.1 | 0 | P = 0.051477 vs Vehicle (PBS) |

As shown in FIG. 3 and Table 7A and Table 7B, at the end of the experiment, the body weight of mice in the PBS group decreased by 16% and 3% over the course of the experiment. The group of mice administered Taxol (10 mg/kg) gained about 7-15% body weight over the course of the experiment. The Compound 5 (9.6 mg/kg, equimolar to 2.5 mg/kg Taxol) group had no change in body weight over the course of the experiment. The body weight of mice in the Compound 3 group (9.6 mg/kg, equimolar to 2.5 mg/kg Taxol) increased by about 13%. Compared with those in the vehicle (PBS) group, the weight was about 24% higher.

In separate experiment where the influence on body weight of 38.4 mg/kg Compound 3 and Compound 5 were evaluated, tumor bearing mice were treated with 38.4 mg/kg Compound 3 or Compound 5. after 3 Q5D doses. On Day 21, the body weight change of Compound 3 treated mice were +22.1%, where that of Compound 5 treated mice were −2%. The mice treated with Compound 5 were recumbent and their voluntary activities were reduced. A few hours after the completion of administration, they were generally in good condition and had a normal appetite. One mouse in this group was found dead on Day 18. When mice were treated with Compound 3 (38.4 mg/kg), no animal deaths were reported during the experiment.

The safety profile of Compound 3 was better than that of Compound 5. After treating the animals with three doses of Compound 5, the mice showed little to no body weight increase. However, mice showed increased body weight after Compound 3 treatment, which indicates a better recovery or therapeutic response of these animals. The higher the elimination and/or reduction of the tumors, the better the outcome for survival and weight gain. The increase in body weight after treatment with Compound 3 was similar to that of the proved drug Taxol (paclitaxel).

Biological Example 6

Efficacy in Metastatic Ovarian Cancer Model

Method: The method was the same as described for Biological Example 4. Groups of 12 animals (12 animals in each group) were administered an intraperitoneal (IP) dose of either Taxol (10 mg/kg), Compound 3 (9.6 mg/kg, equimolar to 2.5 mg/kg Taxol), or Compound 5 (9.6 mg/kg, equimolar to 2.5 mg/kg Taxol).

Tumor progression in each group: Images of tumor growth and progression were acquired three times a week during the period of the study with the FluorVivo imaging system, Model 100/Mag (INDEC, CA, USA) and the average tumor area of each group was calculated according to the results of image analysis.

Endpoint tumor load of each group: At Day 21 after administration, the tumor load of each group was calculated by dissecting and weighing the tumor in the abdominal cavity. The results are shown in Table 8A and Table 8B. Both compounds were separately compared to Taxol as shown in Table 8A and Table 8B. The vehicle was the control.

TABLE 8A

Average Tumor Area following Administration with Compound 3

| Groups | Average tumor area on day 0 (MEAN ± SD) | Average tumor area on day 21 (MEAN ± SD) | P value |
|---|---|---|---|
| Vehicle (PBS) | 18.9 ± 3.9 | 173.4 ± 66.9 | |
| Taxol (10 mg/kg) | 18.4 ± 3.3 | 24.8 ± 27.1 | P = 0.00050396 vs Vehicle (PBS); |
| Compd 3 (9.6 mg/kg, equimolar to 2.5 mg/kg Taxol) | 18.6 ± 5.3 | 30.9 ± 24.2 | P = 0.00061669 vs Vehicle (PBS); P = 0.68918128 vs Taxol (10 mg/kg) |

TABLE 8B

Average Tumor Area following Administration with Compound 5

| Groups | Average tumor area on day 0 (MEAN ± SD) | Average tumor area on day 21 (MEAN ± SD) | P value |
|---|---|---|---|
| Vehicle (PBS) | 22.0 ± 3.8 | 287.8 ± 23.9 | |
| Taxol (10 mg/kg) | 22.8 ± 4.1 | 22.7 ± 15.5 | P = 0.000002 vs Vehicle (PBS); |
| Compd 5 (9.6 mg/kg, equimolar to 2.5 mg/kg Taxol) | 24.9 ± 6.6 | 28.7 ± 19.8 | P = 0.000002 vs Vehicle (PBS); |

As shown in Table 8A and Table 8B, on Day 21, the mean tumor fluorescence area of the Taxol (10 mg/kg) groups was about 8-16% of the Vehicle (PBS) group (P=0.000002 in the Compound 5 set of experiments and P=0.00050396 in the Compound 3 set of experiments). Average tumor fluorescence area for the group administered 9.6 mg/kg of Compound 5 (equimolar to 2.5 mg/kg Taxol) was 10% of the respective Vehicle (PBS) group, respectively, and there were statistically significant differences compared to the Vehicle (PBS) groups (P=0.000002). Compound 5 showed good tumor inhibitory effect on peritoneal disseminated human ovarian cancer mice model, but one animal died at Day 18 before the end of the experiment.

Figure 4:
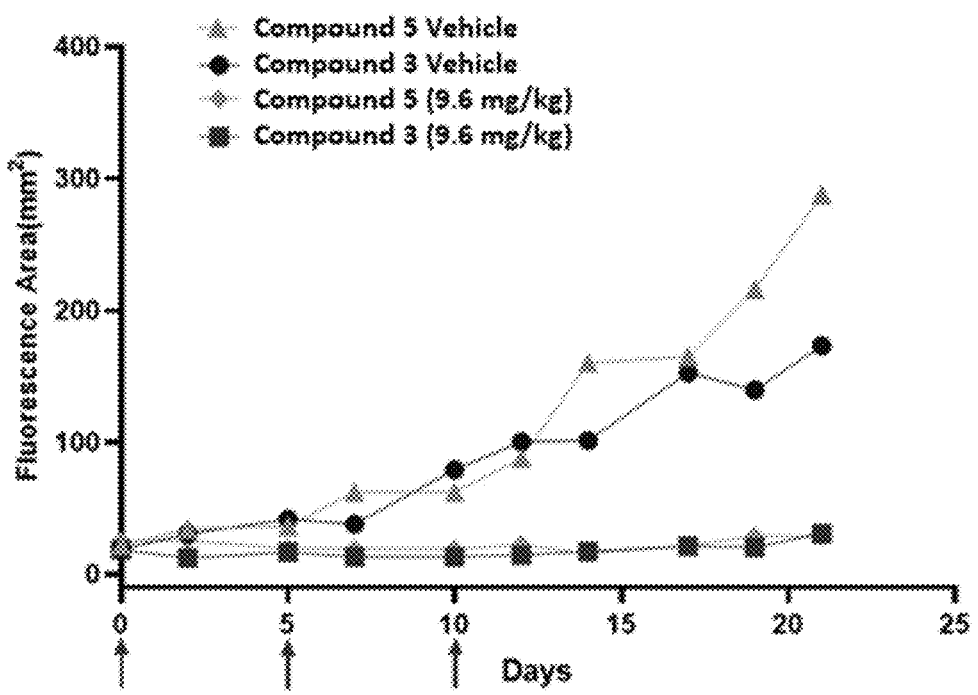
FIG. 4 is a graph of the fluorescence area of the tumor, which is an indicator of tumor growth, during and following administration of Compound 5 or Compound 3. Compound 5 or Compound 3 were administered at time points 0, 5, and 10 as indicated by the arrows and were compared to vehicle as described in Biological Example 6.

The average tumor fluorescence area of the group of Compound 3 was about 20% of the Vehicle (PBS) groups and there was a statistically significant difference between the Compound 3 and Vehicle groups (P=0.00000215). The average tumor fluorescence area of the three groups of mice administered Compound 3 (9.6 mg/kg, equimolar to 2.5 mg/kg Taxol) was about 100% of the Taxol (10 mg/kg) group, and the average tumor weights of mice in the three groups administered Compound 3 was not significantly different from that in the Taxol (10 mg/kg) group. The average fluorescence area is also shown in FIG. 4.

Figure 5:
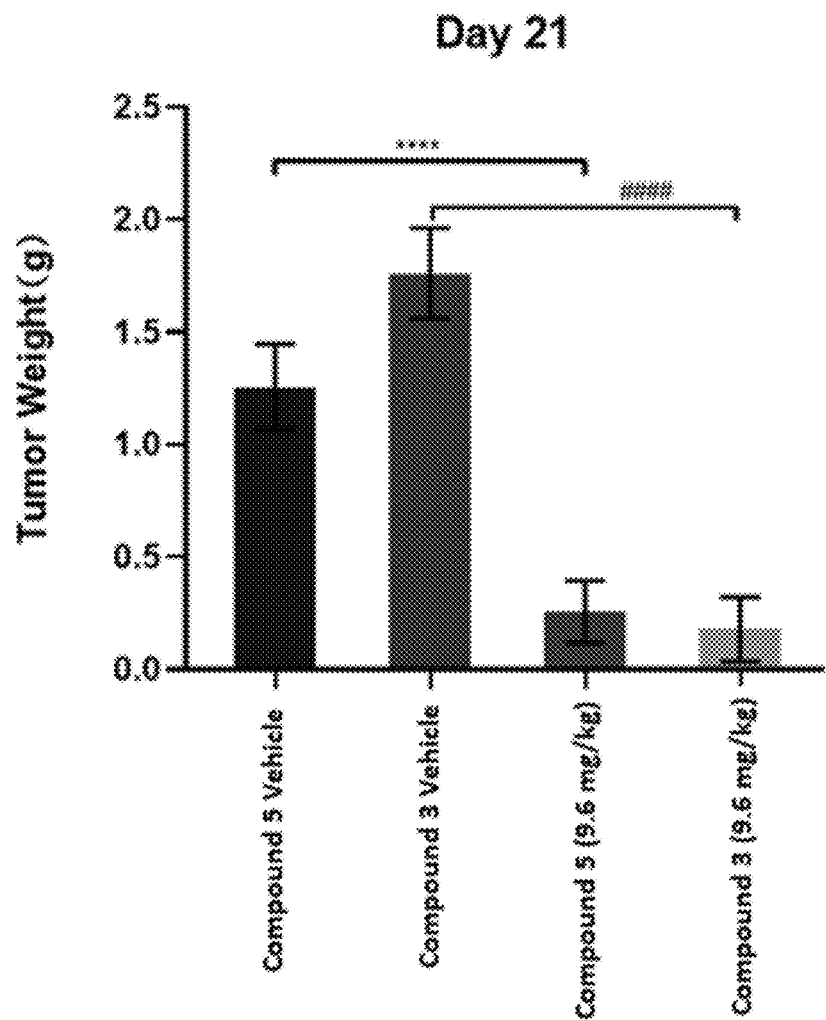
FIG. 5 is a graph of the average tumor weight on Day 21 following administration of Compound 5 or Compound 3. The tumor weight was compared to vehicle as described in Biological Example 6.

The average tumor weight of Compound 3 (9.6 mg/kg, equimolar to 2.5 mg/kg Taxol) groups was about 10% of the Vehicle group and within the same range of the Taxol (10 mg/kg) group. Notably, there was no statistically significant difference in the average tumor weight of mice in the Compound 3-dosed group (9.6 mg/kg, equimolar to 2.5 mg/kg Taxol) compared with the Taxol (10 mg/kg) group. Taxol and Compound 3 showed comparable tumor inhibitory effect, whereas Compound 5 was about 10% less effective than Taxol. Compound 3 showed at least 10% better tumor inhibition effect than Compound 5. FIG. 5 is a graph of the average tumor weight on Day 21 for the Compound 3- and Compound 5-dosed groups compared to their respective vehicles. The results are also shown in Table 9A and Table 9B.

Figure 6A:
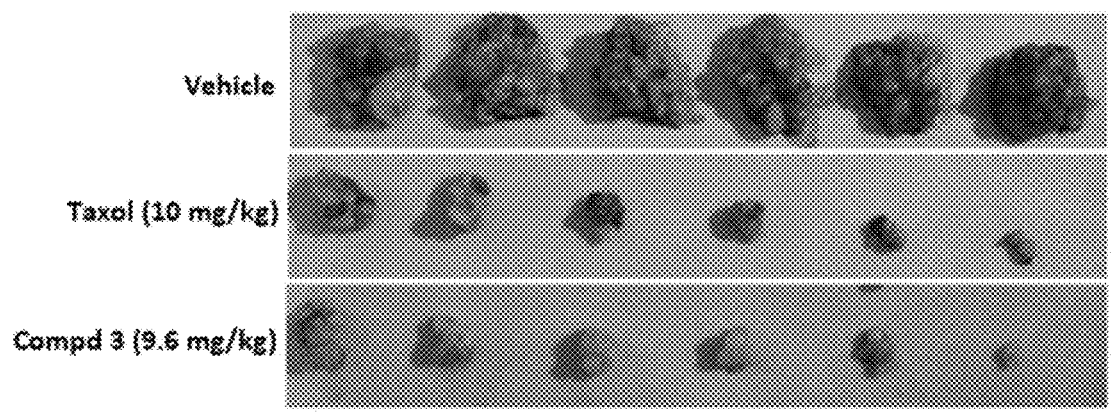
FIG. 6A are images of tumors removed from mice administered vehicle, Taxol (10 mg/kg), or Compound 3 (9.6 mg/kg, equimolar to 2.5 mg/kg). The tumors were removed from six mice in each group on day 21 of the 21-Day experiment as described in Biological Example 6.
Figure 6B:
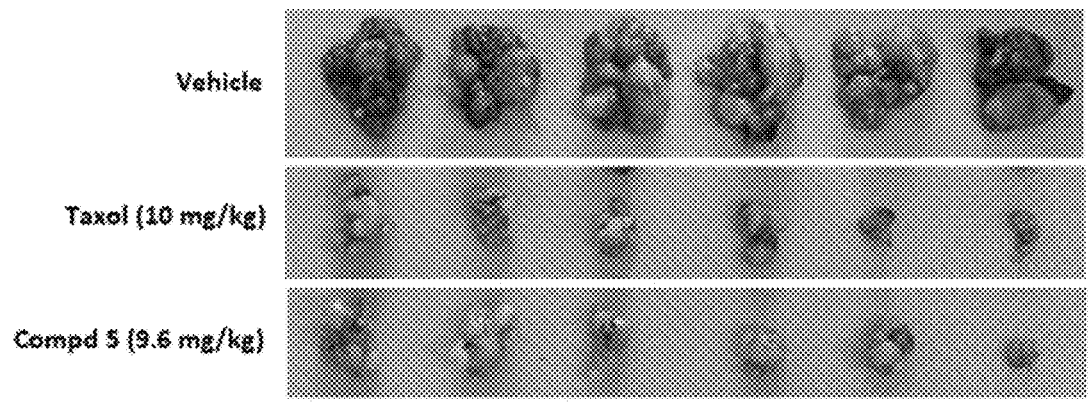
FIG. 6B are images of tumors removed from mice administered vehicle, Taxol (10 mg/kg), or Compound 5 (9.6 mg/kg, equimolar to 2.5 mg/kg). The tumors were removed from six mice in each group on day 21 of the 21-Day experiment as described in Biological Example 6.
Figure 7:
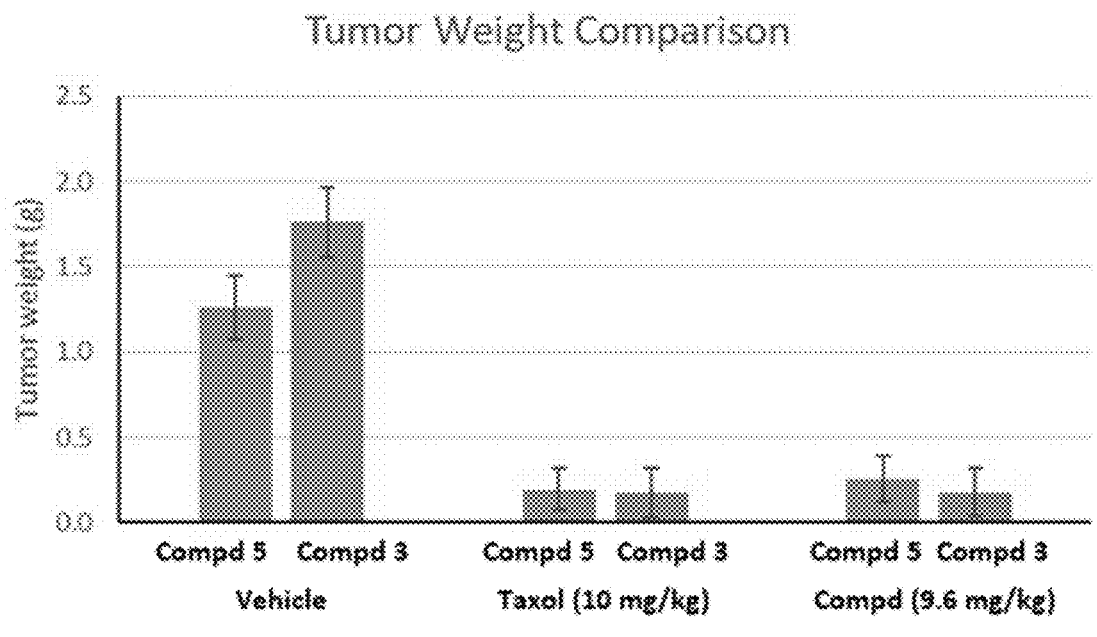
FIG. 7 is a tumor weight comparison graph. All tumors were obtained after the last day of the experiment. As described in Biological Example 6, mice administered Compound 5 and Compound 3 were separately compared to mice administered Taxol and vehicle.

FIG. 6A and FIG. 6B are photographic images of the removed tumors for the Compound 3- and Compound 5-dosed groups compared to their respective vehicles and Taxol. Tumors from 6 mice in each groups are shown in FIG. 6A and FIG. 6B. FIG. 7 is a graph comparing Compound 3 and Compound 5 to their respective Taxol and Vehicle groups.

TABLE 9A

Mean Tumor Mass following Administration of Compound 3

| Groups | Mean tumor mass (g) (MEAN ± SD) | P value |
|---|---|---|
| Vehicle (PBS) | 1.760 ± 0.200 | |
| Taxol (10 mg/kg) | 0.174 ± 0.141 | P = 0.00000002 vs Vehicle (PBS) |
| Compd 5 (9.6 mg/kg, equimolar to 2.5 mg/kg Taxol) | 0.178 ± 0.143 | P = 0.00000002 vs Vehicle (PBS) |

TABLE 9B

Mean Tumor Mass following Administration of Compound 5

| Group | Mean tumor mass (g) (MEAN ± SD) | P value |
|---|---|---|
| Vehicle (PBS) | 1.2557 ± 0.1893 | |
| Taxol (10 mg/kg) | 0.1970 ± 0.1248 | P = 0.000011 vs Vehicle (PBS) |
| Compd 3 (9.6 mg/kg, equimolar to 2.5 mg/kg Taxol) | 0.25550 ± 0.1388 | P = 0.000013 vs Vehicle (PBS) |

Tumor inhibitory rate (IR): Tumor IR was calculated based on the final average tumor weights according to the formula:

$$IR\ (\%) = (1 - treatment(t)/control(c)) \times 100$$

Figure 8:
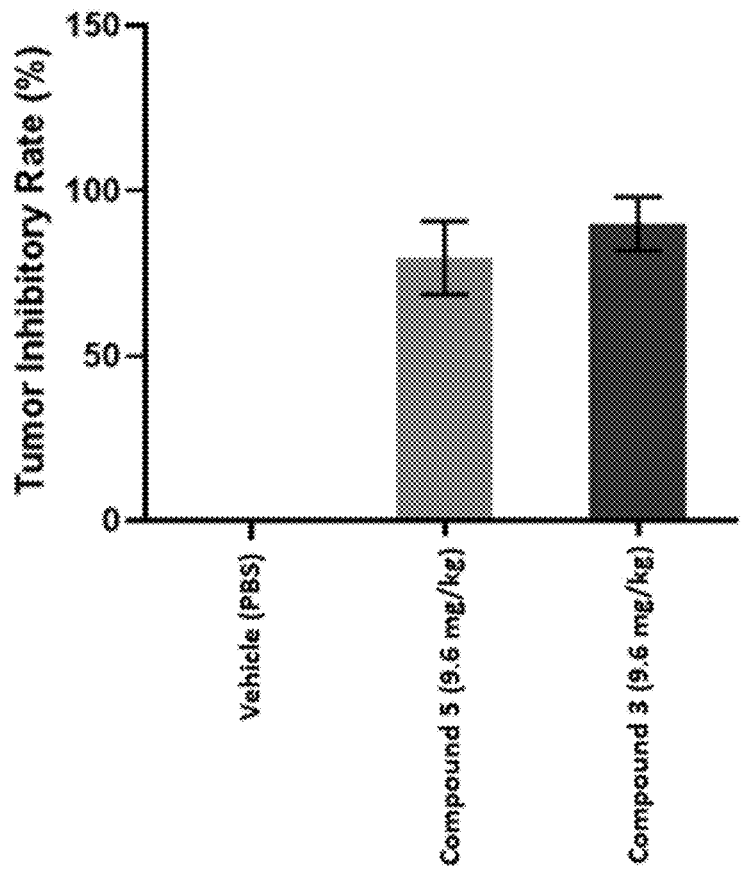
FIG. 8 is a graph comparing the tumor inhibitory rate (IR) of mice administered Compound 5 and Compound 3 as described in Biological Example 6.
Figure 9:
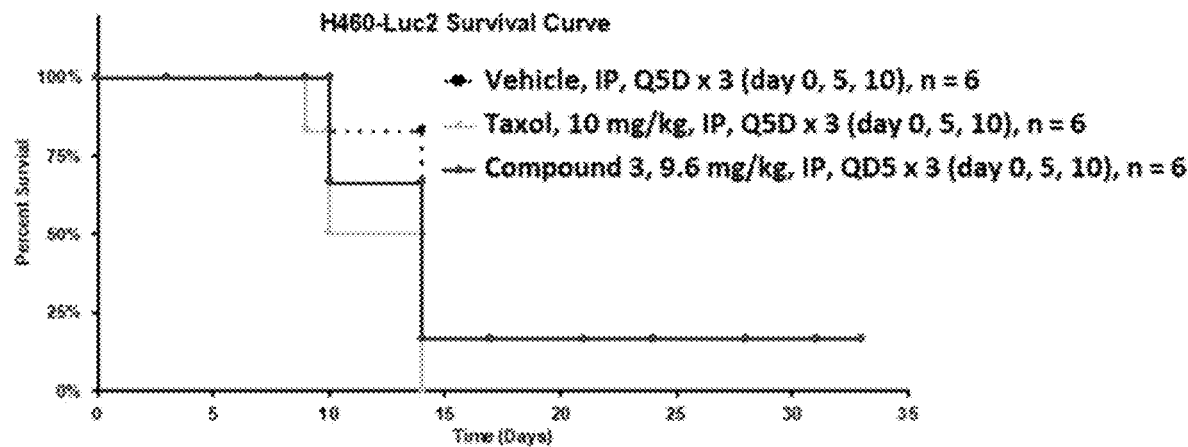
FIG. 9 are the Kaplan-Meier survival curves of Compound 3-treated, vehicle-treated, and Taxol-treated NCI-H460-luc2 intracranial model in female BALB/c nude mice as described in Biological Example 7.

FIG. 8 and Table 10A and Table 10B show the average IR in each group at the end of the experiment.

TABLE 10A

Tumor inhibitory rate of Mice Administered Compound 3

| Groups | Average tumor inhibitory rate (%) (MEAN ± SD) |
|---|---|
| Vehicle (PBS) | — |
| Taxol (10 mg/kg) | 90 ± 8 |
| Compd 3 (9.6 mg/kg, equimolar to 2.5 mg/kg Taxol) | 90 ± 8 |

TABLE 10B

Tumor inhibitory rate of Mice Administered Compound 5

| Groups | Average tumor inhibitory rate (%) (MEAN ± SD) |
|---|---|
| Vehicle (PBS) | — |
| Taxol (10 mg/kg) | 84 ± 10 |
| Compd 5 (9.6 mg/kg, equimolar to 2.5 mg/kg Taxol) | 79 ± 11 |

The efficacy results of the mouse model of peritoneal dissemination and metastasis model of human ovarian cancer showed that the tumor inhibition effect of Compound 3 was significantly better than that of Compound 5. Tumor inhibitory rates of Compound 5 was 79±11% at 9.6 mg/kg, while that of Compound 3 at 9.6 mg/kg was 90±8%. Under the dose and experimental conditions, Compound 3 had no obvious acute toxic effect on experimental mice, while Compound 5 caused animal death.

Biological Example 7

Efficacy of Compound 3 Against Brain Cancer

Cell Culture: Luciferase marked NCI-H460-luc2 human intracranial cells were maintained in vitro as a monolayer culture in ATCC formulated RPMI1640 medium supplemented with 10% heat inactivated fetal bovine serum, 100 U/mL penicillin and 100 μg/mL streptomycin at 37° C. in an atmosphere of 5% $CO_2$ in air. The tumor cells were routinely subcultured twice weekly by trypsin-EDTA treatment. The cells growing in an exponential growth phase were harvested and counted for tumor inoculation.

Tumor Inoculation and Animal Grouping: Female BALB/c nude mice were anesthetized with avertin (20 μL/g). The animals were dosed intraperitoneally with 10 mg/kg of carprofen 30 minutes post-surgery for pain relief.

The anesthetized mouse was properly positioned. The surgical area was prepped with 70% ethanol solution. Using a sterile scalpel, a sagittal incision was made over the parieto-occipital bone, approximately 1 cm long. The exposed skull surface was then cleaned using a cotton swab soaked in 0.9% saline. Prior to tumor cell injection, a sterile 25 gauge sharp needle was used to puncture the skull at 2 mm to the right of the bregma and 1 mm anterior to the coronal suture, thereby creating an opening for the injection of tumor cells. Prior to drawing cells into the syringe, the contents of the cell suspension was mixed by tapping with finger. The syringe was loaded with the desired amount of cell suspension, and extra care was taken to avoid air bubbles. The outside of syringe was then cleaned with an alcohol swab to wipe the exterior free of any adherent cells, which helped to prevent extracranial tumor establishment and growth. To ensure that the appropriate injection depth was achieved, a 3 mm length was cut off on pointed end of a P20 pipetteman tip by a scalpel. This section of the tip was fitted over the syringe to limit the injection depth, and to ensure that the tip of the syringe needle was 3 mm from the underside of the skull. The syringe was placed perpendicular to the skull, in the hole previously created. And the cell suspension was slowly injected (a 3 μL suspension contains 1×105 NCI-H460-luc2 cells in 20% Matrigel should be injected over a 1 minute period). Intraventricular injection of cells and subsequent spinal dissemination was prevented by appropriate angle of syringe insertion. Upon completion of injection, the needle was left in place for another minute, and then slowly withdrawn. The hole as closed with medical anastomotic glue (OB). Using forceps, the scalp was drawn together over the skull and the incision was closed with surgical suture. The mice were kept warm until completely recovered from anesthesia.

Animals were selected and randomized (based on their bioluminescence density) on day 4 after tumor implantation. Treatment was initiated according to the predetermined regimen as shown in Table 11.

Observations: During routine monitoring, the animals were checked daily for any effects of tumor growth and treatments on normal behavior such as mobility, food and water consumption (by looking only), body weight gain/loss (body weights were measured twice weekly or daily), eye/hair matting and any other abnormal effect stated in the protocol. Death and observed clinical signs were recorded on the basis of the numbers of animals within each subset.

Bioluminescence Measurements and Endpoints: The surgically inoculated mice were weighed and intraperitoneally administered luciferin at a dose of 150 mg/kg. Ten to fifteen minutes after the luciferin injection, the animals were pre-anesthetized with the mixture gas of oxygen and isoflurane. When the animals were in a complete anesthetic state, the mice were moved into the imaging chamber for biolumi-nescence measurements with an IVIS (Lumina II) imaging system.

The major endpoint was to determine if the tumor biolu-minescence growth can be delayed, decreased, or vanished. The body weights were measured twice weekly or once a day when the mice showed obvious morbidity. The biolu-minescence of the whole animal body, including primary and metastatic tumors, was measured and recorded once per week according to protocol (bioluminescence data not shown). Animals showing moribund with obvious body weight loss over 20%, or unreachable diet normally, or paralyzed were defined as dying.

Median survival time (Days) of each group were calculated based on the survival time of the animal within, increased life span (ILS) was analyzed according to the median survival time in treatment groups and vehicle group.

Statistical Analysis: All animals still survived at day 7 post grouping, thus statistical analysis of difference in bioluminescence among the groups was conducted on the data obtained on the 7th day after drug dosing by T-Test. All data analyzed using SPSS 17.0. p<0.05 was considered to be statistically significant.

The survival time was analyzed by Kaplan-Meier method. The event of interest was the animal death. The survival time was defined as the time from the start of dosing to death. For each group, the median survival time and corresponding 95% confidence interval were calculated. The Kaplan-Meier curves were also constructed for each group and the Log-rank test was used to compare survival curves between groups.

Survival Time: The effects of Compound 3 and Paclitaxel (Taxol) treatment on the survival of NCI-H460-luc2 human intracranial model in female BALB/c nude mice were shown in Table 11. At the end point, one mouse in Compound 3 38.4 mg/kg group was still alive.

Figure 11:
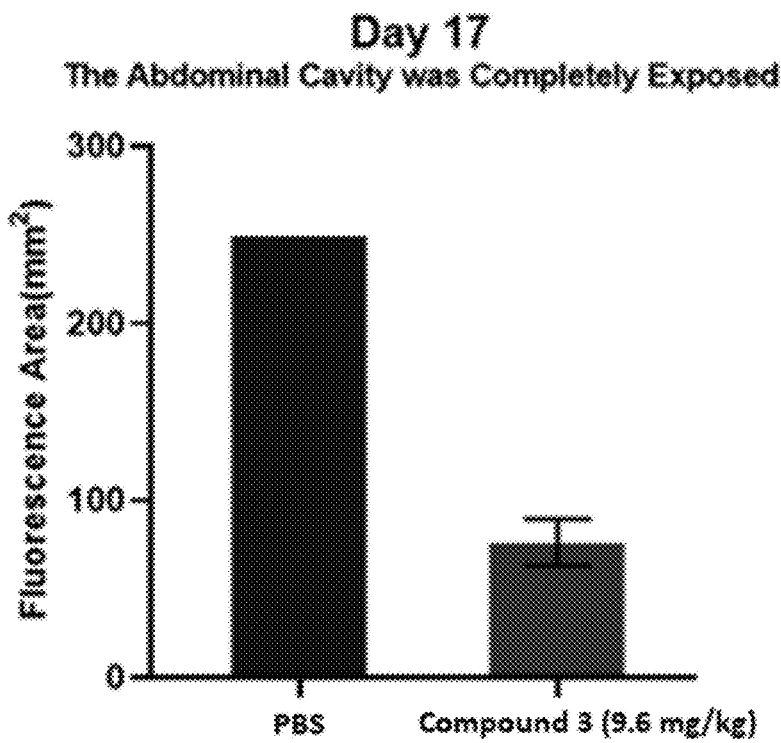
FIG. 11 is a graph comparing the fluorescence area of the tumor on Day 17 of mice administered Compound 3 compared to vehicle as described in Biological Example 8.

Survival for animals in each group is shown in FIG. 11 and Table 11. Median survival time (MST) value of the vehicle group was 14 days. The MST value for Paclitaxel (10 mg/kg) and Compound 3 (38.4 mg/kg) groups were 10 days (95% confidence interval: 7.60-12.40 days) and 14 days (95% confidence interval: 11.61-16.39 days), respectively.

TABLE 11

Effects of Compound 3 and Taxol on the survival time (MST)

| Treatment | Median Survival Time (Days)[a] | 95% Confidence Interval | | Increase Life Span (%) | Log Rank P value[b] | Log Rank P value[c] | Log Rank P value[d] | Log Rank P value[e] |
|---|---|---|---|---|---|---|---|---|
| | | Lower Bound | Upper Bound | | | | | |
| Vehicle | 14 | N/A | N/A | — | — | — | — | — |
| Paclitaxel 10 mg/kg | 10 ± 1 | 7.60 | 12.40 | −28.57 | 0.292 | — | — | — |
| Compound 3 9.6 mg/kg | 14 | N/A | N/A | 0.00 | 0.624 | 0.483 | — | — |
| Compound 3 19.2 mg/kg | 10 ± 2 | 6.00 | 14.00 | −28.57 | 0.124 | 0.647 | 0.250 | — |
| Compound 3 38.4 mg/kg | 14 ± 1 | 11.61 | 16.39 | 0.00 | 0.880 | 0.309 | 0.613 | 0.182 |

[a]Medium Survival Time (MST) ± SEM.
[b]p value was obtained by comparison of treatment groups with vehicle group.
[c]p value was obtained by comparison of treatment groups with Paclitaxel 10 mg/kg group.
[d]p value was obtained by comparison of treatment groups with Compound 3 9.6 mg/kg group.
[e]p value was obtained by comparison of treatment groups with Compound 3 19.2 mg/kg group.

Biological Example 8

Efficacy of Compound 3 Against Pancreatic Cancer

Figure 10:
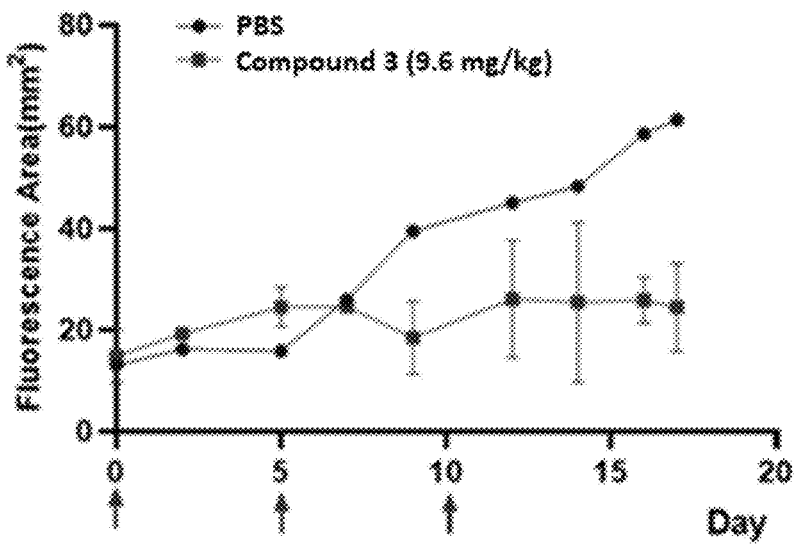
FIG. 10 is a graph of the fluorescence area of the tumor, which is an indicator of tumor growth, during and following administration of Compound 3. Compound 3 was administered at time points 0, 5, and 10 as indicated by the arrows and was compared to vehicle as described in Biological Example 8.
Figure 12:
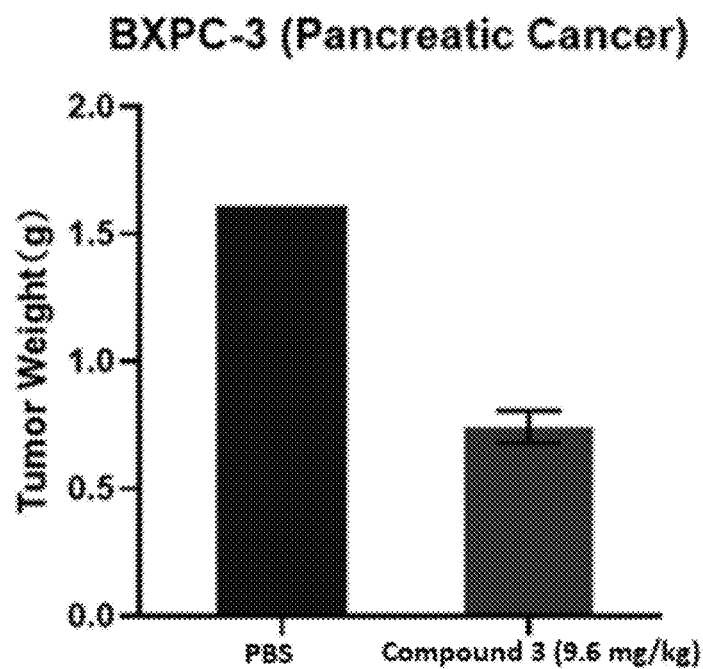
FIG. 12 is a graph of the average tumor weight on Day 17 following administration of Compound 3. The tumor weight was compared to vehicle as described in Biological Example 8.

Following the procedure described in Biological Example 5, mice were injected with human pancreatic cancer (BXPC-3) cells and treated with Compound 3 (9.6 mg/kg) QD5 (dosing on days 0, 5, and 10) to study the efficacy of Compound 3. The fluorescence area of the tumor was measured over the course of the study, and as shown in FIG. 10, the fluorescence area increased in the vehicle-administered mice to a greater degree over the course of the study compared to the Compound 3-administered mice. FIG. 11 is a graph comparing the fluorescence area on Day 17 of the study of the mice administered vehicle and the mice administered Compound 3. FIG. 12 is a graph comparing the tumor weight of the mice administered vehicle and the mice administered Compound 3 on Day 17.

Biological Example 9

Efficacy of Compound 3 Against Gastric Cancer

Figure 13:
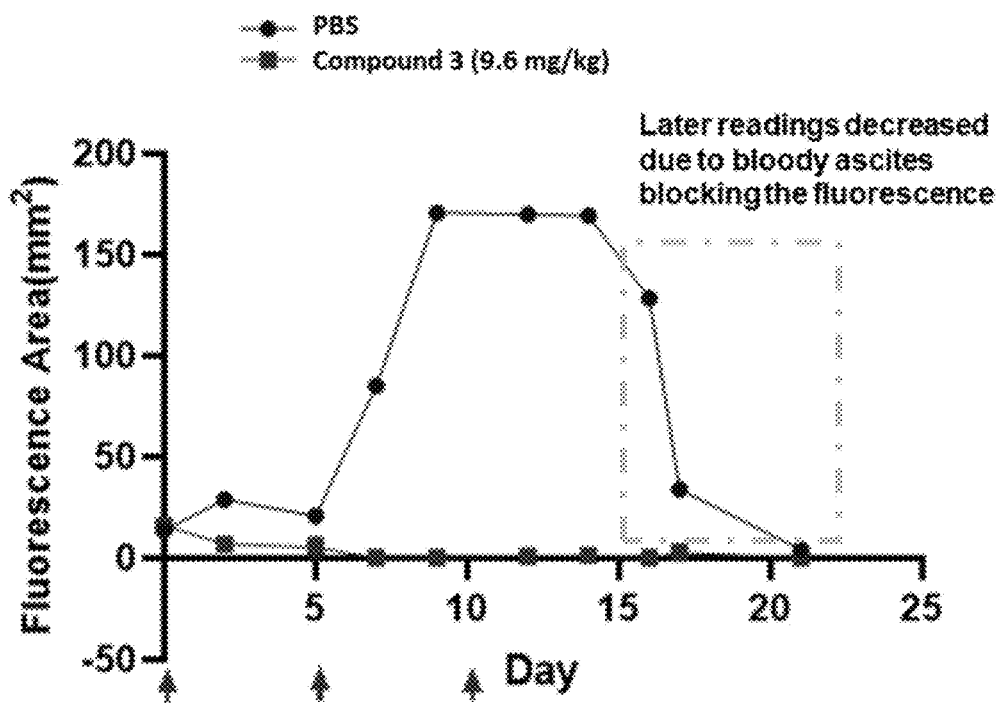
FIG. 13 is a graph of the fluorescence area of the tumor, which is an indicator of tumor growth, during and following administration of Compound 3. Compound 3 was administered at time points 0, 5, and 10 as indicated by the arrows and was compared to vehicle as described in Biological Example 9.
Figure 14:
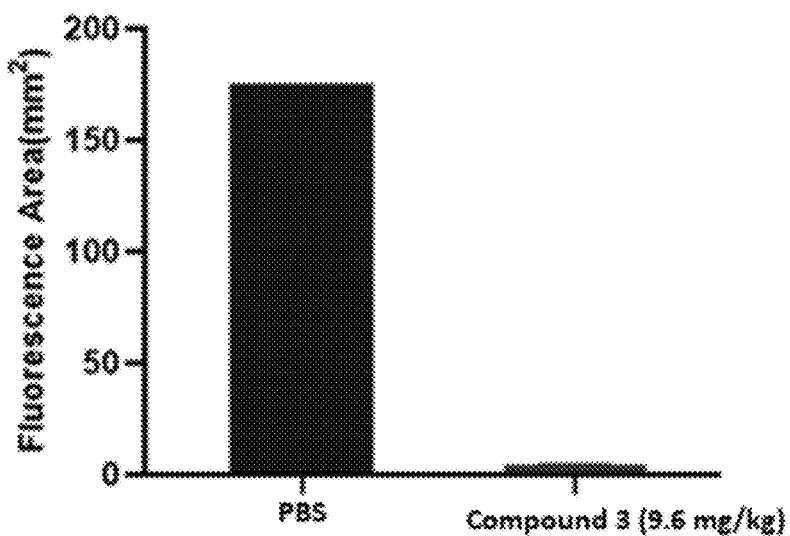
FIG. 14 is a graph comparing the fluorescence area of the tumor on Day 21 of mice administered Compound 3 compared to vehicle as described in Biological Example 9.
Figure 15:
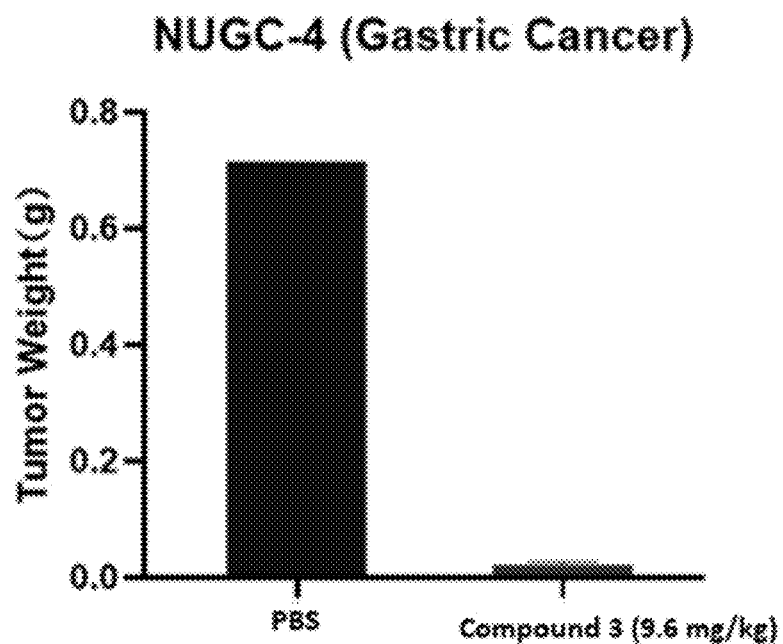
FIG. 15 is a graph of the average tumor weight on Day 21 following administration of Compound 3. The tumor weight was compared to vehicle as described in Biological Example 9.

Following the procedure described in Biological Example 5, mice were injected with human gastric cancer (NUGC-4) cells and treated with Compound 3 (9.6 mg/kg, equimolar to 2.5 mg/kg Taxol) QD5 (dosing on days 0, 5, and 10) to study the efficacy of Compound 3. The fluorescence area of the tumor was measured over the course of the study (FIG. 13). After approximately Day 15 in the mice administered PBS, the formation of bloody ascites blocked the fluorescence reading. In the mice administered Compound 3, the fluorescence decreased over the course of the study. FIG. 14 is a graph comparing the fluorescence area on Day 21 of the study of the mice administered vehicle and the mice administered Compound 3. FIG. 15 is a graph comparing the tumor weight of the mice administered vehicle and the mice administered Compound 3 on Day 21.

Biological Example 10

Elimination of Ascites

Following the procedure described in Example 5, mice injected with SKOV-3-GFP cells (a cell suspension of $6\times10^6/120$ μL/mouse or $8\times10^6/120$ μL/mouse injected into the peritoneal cavity) were also studied for the formation of ascites. Mice were administered vehicle (PBS), Taxol (10 mg/kg), or Compound 3 (9.6 mg/kg). In the Compound 3 treated mice, no bloody ascites were observed. The PBS groups and the Taxol groups observed formation of malignant as cites in animals.

Figure 16:
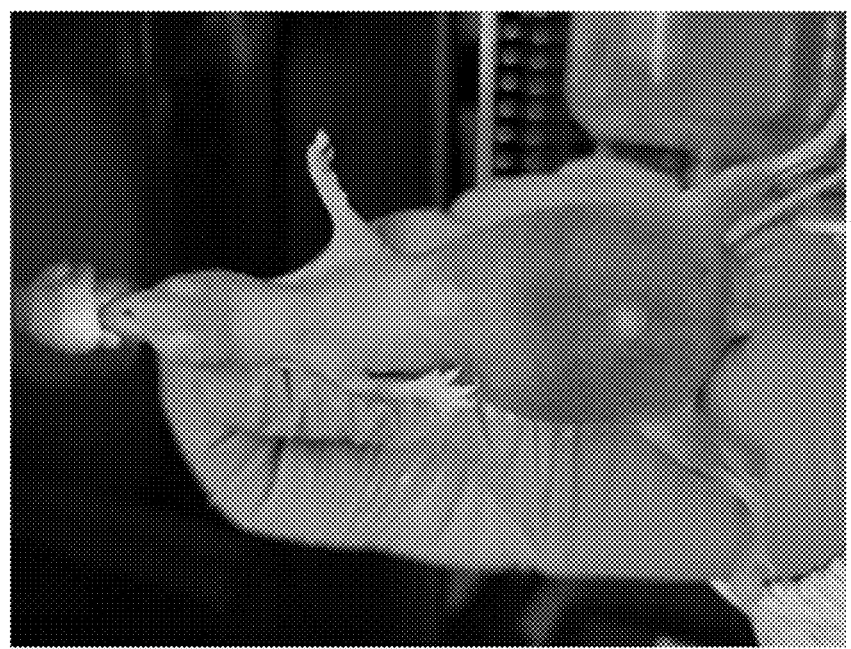
FIG. 16 is an image of the formation of ascites in a mice administered vehicle (PBS) following an injection of SKOV-3-GFP cells ($6\times10^6$/120 μL/mouse) as described in Biological Example 10.
Figure 17A:
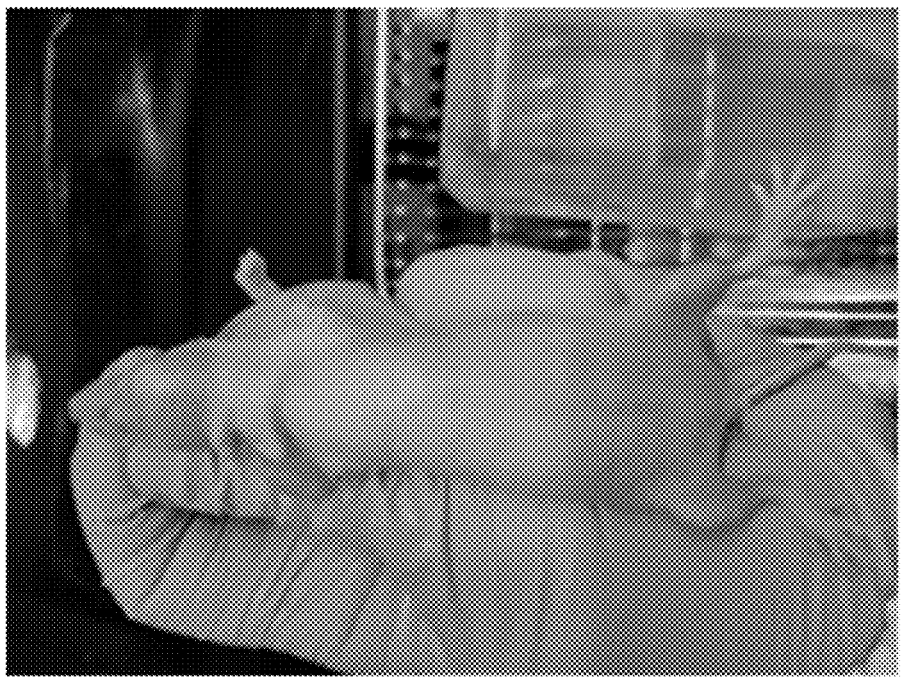
FIG. 17A is an image of a mice administered Compound 3 (9.6 mg/kg) following an injection of SKOV-3-GFP cells ($6\times10^6$/120 μL/mouse) as described in Biological Example 10. No bloody ascites were observed.
Figure 17B:
FIG. 17B is an image of a mice administered Compound 3 (9.6 mg/kg, equimolar to 2.5 mg/kg Taxol) following an injection of SKOV-3-GFP cells ($6\times10^6$/120 μL/mouse) as described in Biological Example 10. No bloody ascites were observed.
Figure 18:
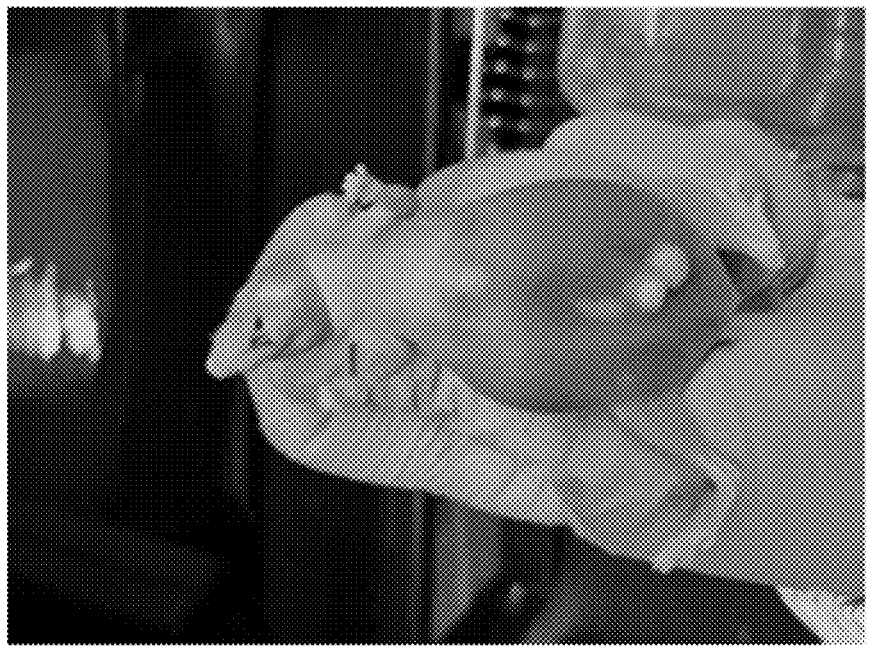
FIG. 18 is an image of the formation of ascites in a mice administered vehicle (PBS) following an injection of SKOV-3-GFP cells ($8\times10^6$/120 μL/mouse) as described in Biological Example 10.
Figure 19:
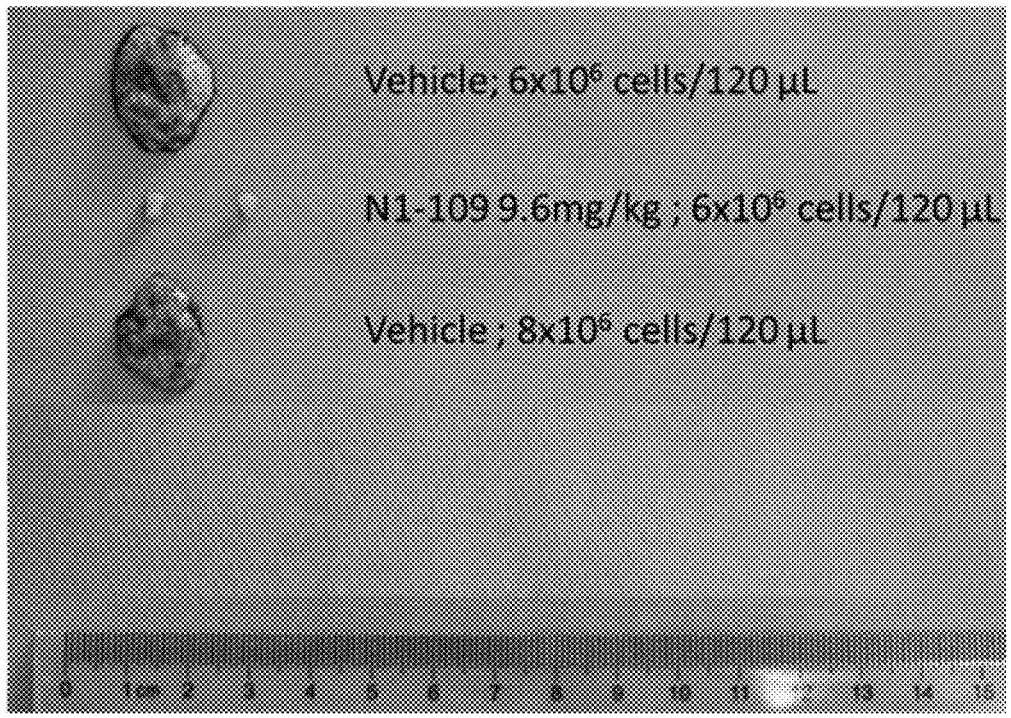
FIG. 19 is an image comparing the ascites removed from the vehicle-administered mice and the Compound 3-administered mice. As described in Biological Example 10, mice were administered vehicle following an injection SKOV-3-GFP cells ($6\times10^6$/120 μL/mouse or $8\times10^6$/120 μL/mouse) or mice were administered Compound 3 (9.6 mg/kg, equimolar to 2.5 mg/kg Taxol) following an injection of SKOV-3-GFP cells ($6\times10^6$/120 μL/mouse). The ascites removed from the vehicle-administered mice were larger and bloody compared to the ascites removed the mice administered Compound 3.

FIG. 16 and FIG. 18 are images of mice administered vehicle following an injection of SKOV-3-GFP cells ($6\times10^6/120$ μL/mouse or $8\times10^6/120$ μL/mouse, respectively). As shown, bloody ascites were observed. FIG. 17A and FIG. 17B are images of two mice administered Compound 3 (9.6 mg/kg, equimolar to 2.5 mg/kg Taxol) following an injection of SKOV GFP cells ($6\times10^6/120$ μL/mouse). As shown, no bloody ascites were observed. FIG. 19 is a comparison of the ascites removed from the mice administered vehicle or Compound 3. As shown in FIG. 19, bloody ascites were removed from the vehicle-administered mice, but not the Compound 3-administered mice.

EQUIVALENTS

The disclosure set forth above may encompass multiple distinct embodiments with independent utility. Although each of these embodiments has been disclosed, the specific embodiments thereof as disclosed and illustrated herein are not to be considered in a limiting sense, because numerous variations are possible. The subject matter of the embodiments includes all novel and nonobvious combinations and subcombinations of the various elements, features, functions, and/or properties disclosed herein. The following claims particularly point out certain combinations and sub-combinations regarded as novel and nonobvious. Alternative embodiments as in other combinations and subcombinations of features, functions, elements, and/or properties may be claimed in this application, in applications claiming priority from this application, or in related applications. Such claims, whether directed to a different embodiment or to the same embodiment, and whether broader, narrower, equal, or different in scope in comparison to the original claims, also are regarded as included within the subject matter of this disclosure.

One or more features from any embodiments described herein or in the figures may be combined with one or more features of any other embodiments described herein or in the figures without departing from the scope of this disclosure.

All publications, patents and patent applications cited in this specification are herein incorporated by reference as if each individual publication or patent application were specifically and individually indicated to be incorporated by reference. Although the foregoing disclosure has been described in some detail by way of illustration and example for purposes of clarity of understanding, it will be readily apparent to those of ordinary skill in the art in light of the teachings of this disclosure that certain changes and modifications may be made thereto without departing from the spirit or scope of the appended claims.

What is claimed is:

1. A compound of Formula (X), or a pharmaceutically acceptable salt thereof:

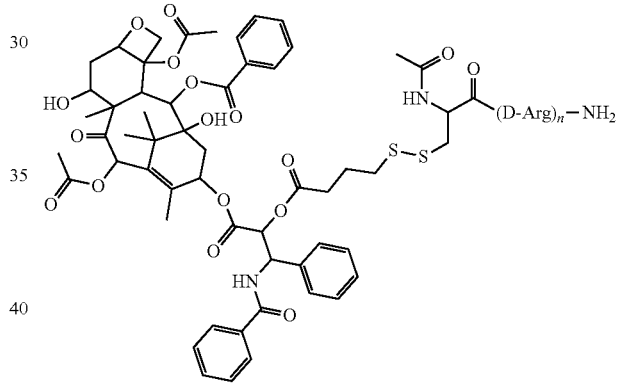

wherein the compound of Formula (X) comprises about 50%, about 60%, about 70%, about 75%, about 80%, about 85%, about 90%, about 95%, or about 99% by weight a stereoisomeric compound of Formula (I):

(I)

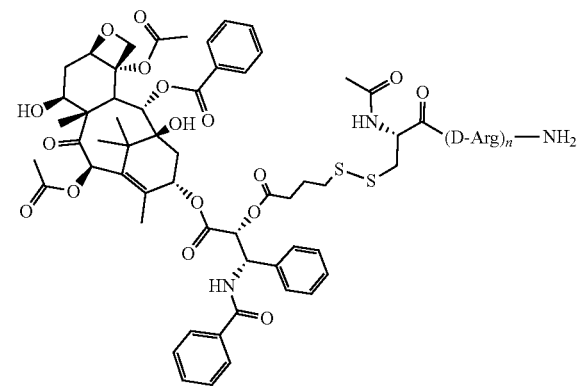

compared to the total weight of all stereoisomers of Formula (X);

wherein n is an integer selected from 1-20.

2. The compound claim 1, wherein the compound of Formula (X) comprises about 90% by weight the stereoisomeric compound of Formula (I).

3. The compound of claim 1, wherein the compound of Formula (X) comprises about 95% by weight the stereoisomeric compound of Formula (I).

4. The compound of claim 1, wherein the compound of Formula (X) comprises about 99% by weight the stereoisomeric compound of Formula (I).

5. A compound of Formula (I), or a pharmaceutically acceptable salt thereof:

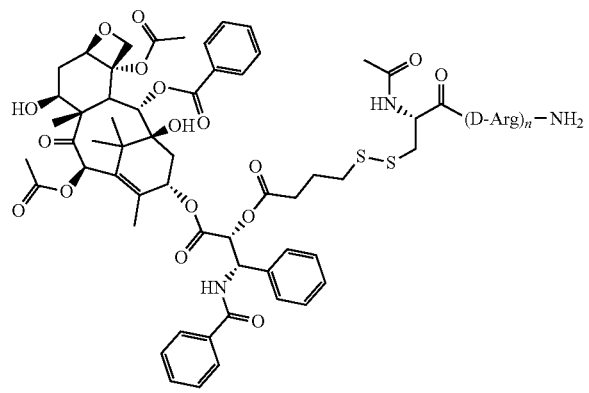

(I)

wherein n is an integer selected from 1-20.

6. The compound of claim 5, wherein the compound is in diastereomeric excess.

7. The compound of claim 6, wherein the compound is in a diastereomeric excess of at least about 50%, 60%, 70%, 75%, 80%, 85%, 90%, 95%, or 99%.

8. The compound of claim 5, wherein the compound is at least about 50% free, at least about 60% free, at least about 70% free, at least about 75% free, at least about 80% free, at least about 85% free, at least about 90% free, at least about 95% free, at least about 97% free, at least about 99% free, or 100% free by weight of the opposite D-cysteine amino acid epimer.

9. The compound of claim 8, wherein the compound is at least about 90% free by weight of the opposite D-cysteine amino acid epimer.

10. The compound of claim 8, wherein the compound is at least about 95% free by weight of the opposite D-cysteine amino acid epimer.

11. The compound of claim 8, wherein the compound is at least about 97% free by weight of the opposite D-cysteine amino acid epimer.

12. The compound of claim 1, wherein n is an integer from 6-10.

13. The compound of claim 1, wherein n is 8.

14. The compound of claim 1, wherein the compound is according to Formula (II), or a pharmaceutically acceptable salt thereof:

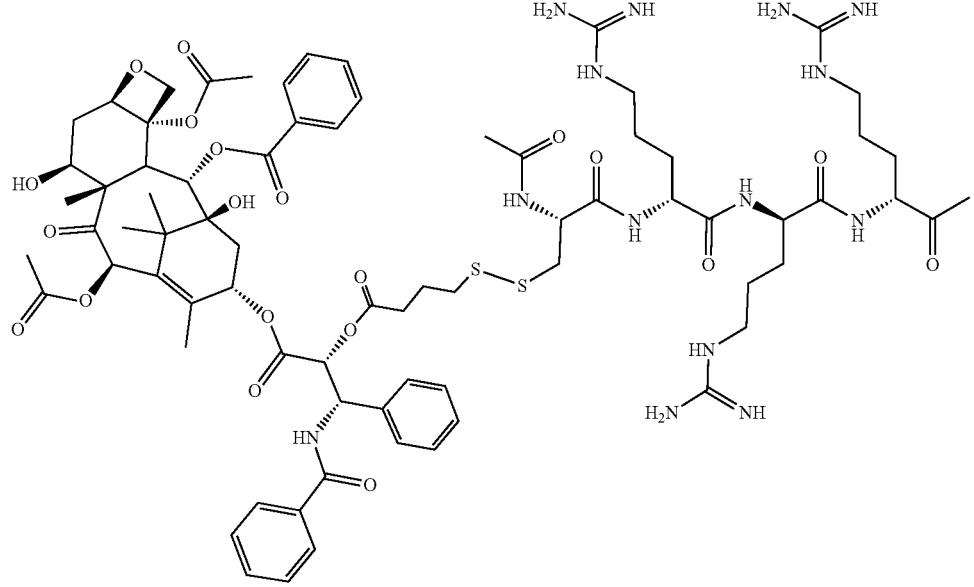

(II)

-continued

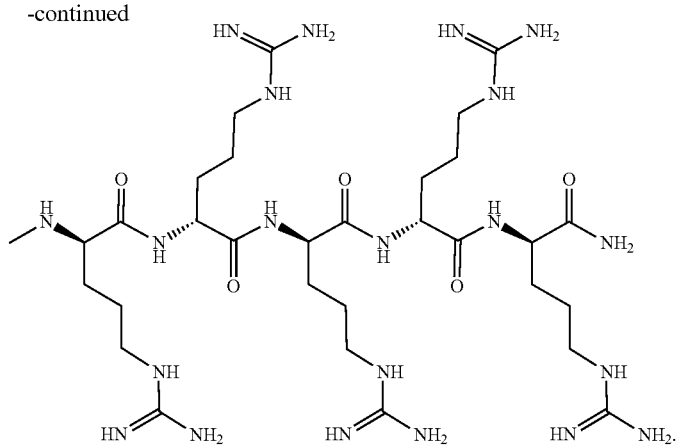

15. The compound of claim 14, wherein the compound is at least about 50% free, at least about 60% free, at least about 70% free, at least about 75% free, at least about 80% free, at least about 85% free, at least about 90% free, at least about 95% free, at least about 97% free, at least about 99% free, or 100% free by weight of the opposite D-cysteine amino acid epimer.

16. The compound of claim 15, wherein the compound is at least about 90% free by weight of the opposite D-cysteine amino acid epimer.

17. The compound of claim 15, wherein the compound is at least about 95% free by weight of the opposite D-cysteine amino acid epimer.

18. The compound of claim 1, which is a pharmaceutically acceptable salt.

19. The compound of claim 18, which is an HCl salt.

20. The compound of claim 18, which is a TFA salt.

21. A composition comprising the compound of Formula (X) of claim 1.

22. A pharmaceutical composition comprising the compound of claim 1, or a pharmaceutically acceptable salt thereof, and one, or more pharmaceutically acceptable carriers, excipients, or diluents.

23. A method of treating a proliferative, dermatological, or ophthalmological disease comprising the step of administering to a patient in need thereof a therapeutically effective amount of a compound of claim 1, optionally in a pharmaceutically acceptable carrier, excipient, or diluent.

24. The method of claim 23, wherein the disease is brain cancer, liver cancer, ovarian cancer, gastric cancer, or colorectal cancer.

25. The method of claim 23, wherein the disease is head and neck cancer, oral cancer, or maxillofacial cancer.

26. The method of claim 23, wherein the compound is administered intraperitoneally.

27. The method of claim 26, wherein the compound is administered via inhalation.

28. The method of claim 23, wherein the compound is administered orally.

29. The method of claim 28, wherein the compound is administered sublingually.

* * * * *